(12) United States Patent
Takakura et al.

(10) Patent No.: US 9,139,617 B2
(45) Date of Patent: Sep. 22, 2015

(54) METHOD FOR DETECTING ANTIBODY AGAINST SITH-1 IN BIOLOGICAL SAMPLE

(75) Inventors: Yoshimitsu Takakura, Iwata (JP); Naomi Oka, Iwata (JP); Kazuhiro Kondo, Tokyo (JP); Nobuyuki Kobayashi, Tokyo (JP)

(73) Assignees: JAPAN TOBACCO INC., Tokyo (JP); VIRUS IKAGAKU KENKYUSHO INC., Toyonaka-shi, Osaka (JP)

( * ) Notice: Subject to any disclaimer, the term of this patent is extended or adjusted under 35 U.S.C. 154(b) by 530 days.

(21) Appl. No.: 13/257,754

(22) PCT Filed: Mar. 31, 2010

(86) PCT No.: PCT/JP2010/055884
§ 371 (c)(1),
(2), (4) Date: Sep. 20, 2011

(87) PCT Pub. No.: WO2010/114029
PCT Pub. Date: Oct. 7, 2010

(65) Prior Publication Data
US 2012/0107842 A1 May 3, 2012

(30) Foreign Application Priority Data
Mar. 31, 2009 (JP) .................................. 2009-087816

(51) Int. Cl.
*C07K 14/005* (2006.01)
*G01N 33/569* (2006.01)
*G01N 33/68* (2006.01)

(52) U.S. Cl.
CPC ........ *C07K 14/005* (2013.01); *G01N 33/56994* (2013.01); *G01N 33/6854* (2013.01); *C07K 2319/70* (2013.01);

(Continued)

(58) Field of Classification Search
USPC ............................................ 435/7.1; 436/518
See application file for complete search history.

(56) References Cited

U.S. PATENT DOCUMENTS

| 5,001,049 A | 3/1991 | Klein et al. |
| 7,972,804 B2 * | 7/2011 | Lee et al. .................... 435/7.24 |
| 8,343,727 B2 * | 1/2013 | Takakura et al. .............. 435/7.1 |

(Continued)

FOREIGN PATENT DOCUMENTS

| EP | 2 199 391 A1 | 6/2010 |
| EP | 2 405 268 A1 | 1/2012 |

(Continued)

OTHER PUBLICATIONS

Kobayashi et al. Identification of novel HHV-6 latent protein associated with mood disorders in CFS, depressive disorder, bipolar disorder and HHV-6 encephalopathy. 6th Intl Conference on HHv-6 & 7 Baltimore, MD, USA (Jun. 22, 2008).*

(Continued)

*Primary Examiner* — Gail R Gabel
(74) *Attorney, Agent, or Firm* — Birch, Stewart, Kolasch & Birch, LLP

(57) ABSTRACT

The present invention relates to a method for detecting an antibody against a small protein encoded by the intermediate stage transcript of HHV-6 (SITH-1) in a biological sample. The method of the present invention includes the following steps: 1) providing the SITH-1 protein; 2) binding the SITH-1 protein provided in step 1) to a carrier; and 3) contacting the biological sample with the SITH-1 protein-bound carrier prepared in step 2) to detect the SITH-1 protein antibody.

6 Claims, 7 Drawing Sheets

(52) U.S. Cl.
CPC . *C12N 2710/16522* (2013.01); *G01N 2333/03* (2013.01); *G01N 2469/20* (2013.01)

(56) References Cited

U.S. PATENT DOCUMENTS

| | | | |
|---|---|---|---|
| 8,431,352 B2* | 4/2013 | Kondo et al. | 435/7.21 |
| 2008/0176340 A1* | 7/2008 | Soldo et al. | 436/518 |
| 2008/0227111 A1 | 9/2008 | Ichii et al. | |
| 2010/0311076 A1 | 12/2010 | Takakura et al. | |
| 2012/0269824 A1* | 10/2012 | Varnum et al. | 424/172.1 |

FOREIGN PATENT DOCUMENTS

| | | |
|---|---|---|
| JP | 2-233697 A | 9/1990 |
| JP | 8-43392 A | 2/1996 |
| JP | 2004-301646 A | 10/2004 |
| JP | 2008-261641 A | 10/2008 |
| WO | WO 2009/028625 A1 | 3/2009 |
| WO | WO 2009/041501 A1 | 4/2009 |
| WO | WO 2010/101157 A1 | 9/2010 |

OTHER PUBLICATIONS

Dominguez et al., "Human Herpesvirus 6B Genome Sequence: Coding Content and Comparison with Human Herpesvirus 6A," Journal of Virology (Oct. 1999), vol. 73, No. 10, pp. 8040-8052.

Extended European Search Report issued May 3, 2012, in European Patent Application No. 10758600.6.

International Search Report issued Jun. 29, 2010, in PCT International Application No. PCT/JP2010/055884.

Kobayashi et al., "Identification of novel HHV-6 latent protein associated with mood disorders in CFS . . . ," 6th Intl. Conference on HHV-6 & 7 in Baltimore, MD, USA, Jun. 22, 2008 Dai 56 Kai The Japanese Society of Virology Gakujyutsu Shukai Program, Shorokushu, Oct. 1, 2008, p. 120, 1WSF5.

Kobayashi et al., "Identification of novel HHV-6 latent protein associated with mood disorders in CFS, depressive disorder, bipolar disorder and HHV-6 encephalopathy," Dai 56 Kai The Japanese Society of Virology Gakujyutsu Shukai Program, Shorokushu, Oct. 1, 2008, p. 120, 1WSF5.

Kondo et al., "Association of Human Herpesvirus 6 Infection of the Central Nervous System with Recurrance of Febrile Convulsions," The Journal of Infectious Diseases (1993), vol. 167, pp. 1197-1200.

Kondo et al., "Detection of a Gene Cluster that is Dispensible for Human Herpesvirus 6 Replication and Latency," Journal of Virology (Oct. 2003), vol. 77, No. 19, pp. 10719-10724.

Kondo et al., "Identification of Human Herpesvirus 6 Latency-Associated Transcripts," Journal of Virology (Apr. 2002), vol. 76, No. 8, pp. 4145-4151.

Kondo et al., "Latent human herpesvirus 6 infection of human monocytes/macrophages," Journal of General Virology (1991), vol. 72, pp. 1401-1408.

Kondo et al., "Recognition of a Novel Stage of Betaherpesvirus Latency in Human Herpesvirus 6," Journal of Virology (Feb. 2003), vol. 77, No 3, pp. 2258-2264.

Kondo, K., "Human herpesvirus latency and fatigue," Virus (2005), vol. 55, No. 1, pp. 9-18.

* cited by examiner

METHOD FOR DETECTING ANTIBODY AGAINST SITH-1 IN BIOLOGICAL SAMPLE

TECHNICAL FIELD

The present invention relates to a method for qualitatively and/or quantitatively detecting an antibody against a small protein encoded by the intermediate stage transcript of HHV-6 (SITH-1) in a biological sample. The method of the present invention enables detection of an antibody against the SITH-1 protein which is present in a trace amount in a biological sample and which cannot be readily detected by a conventional process.

BACKGROUND ART

In a virus of the family Herpesviridae, a core protein is surrounded by double-stranded DNA with molecular masses of 80-150×10$^6$ Daltons which is enclosed in an icosahedral capsid with a diameter of about 100 nm which consists of 162 capsomers to form a nucleocapsid which is surrounded by an envelope to have an overall size of ca. 150-200 nm. Herpes viruses have been found in almost all mammals and amphibians and, in particular, viruses of the family Herpesviridae which have host specificity for humans are named human herpesviruses (HHVs). HHVs are classified into subfamilies alpha-herpesvirinae (e.g., herpes simplex virus and varicella zoster herpes virus), beta-herpesvirinae (e.g., cytomegalovirus), and gamma-herpesvirinae (e.g., EB virus).

Such herpes viruses are characterized by "latent infection". The "latent infection" refers to an infection state in which viruses exist without production of infectious virus particles in host cells. In the latent infection, the virus gene and the gene product assisting the existence of the virus gene are retained in the host cells. It is known that herpes viruses under the latent infection are reactivated by any factor of the host, for example, increasing age or deconditioning (e.g. fatigue), so that a large number of viruses are duplicated through restart of production of virus particles (reactivation).

Accordingly, herpes viruses have unique properties; although they continue latent infection as long as the host is normal, they are reactivated to seek any other host if they scent the crisis of the host due to disturbance in the body of the host.

Comprehension on the latent infection and reactivation of viruses are essential for investigation of ecology of viruses of the family Herpesviridae. Unfortunately, sufficient knowledge is given to only the EB virus of the family gamma-herpesvirinae among the herpes viruses, and other viruses remains still unclear.

In particular, no additional information other than knowledge which was previously presented by some of the present inventors is disclosed on factors of beta-herpes viruses which involve latent infection. For example, Non-Patent Literature 1 discloses HHV-6 which is in a state of latent infection in macrophages exhibiting relatively high differentiation in peripheral blood, and also discloses the site of the latent infection with HHV-6 in the host. Non-Patent Literature 2 discloses high-rate transfer of HHV-6 into brain at the initial infection, which causes persistent infection or latent infection. Non-Patent Literature 3 discloses a gene expressed by the latent infection with HHV-6 (latent infection gene) and suggests that the gene controls the latent infection and reactivation of the viruses.

Non-Patent literature 4 shows that the state of latent infection with HHV-6 involves an intermediate stage which is comparatively stable and allows for active gene expression, with a result that a latent infection gene and a protein encoded by this gene (the latent infection gene protein) are expressed abundantly. Furthermore, Non-Patent Literature 5 shows that patients with chronic fatigue syndrome have in their serum antibodies against latent infection gene proteins the expression of which is enhanced at the intermediate stage.

CITATION LIST

Non-Patent Literature

Non-Patent Literature 1: Kondo. K et al. Latent human herpesvirus 6 infection of human monocytes/macrophages, J Gen Virol 72:1401-1408, 1991

Non-patent Literature 2: Kondo. K et al. Association of human herpesvirus 6 infection of the central nervous system with recurrence of febrile convulsions. J Infect Dis 167:1197-1200, 1993

Non-patent Literature 3: Kondo. K et al. Identification of human herpesvirus 6 latency-associated transcripts., J Virol. 76: 4145-4151, 2002

Non-patent Literature 4: Kondo K et al. Recognition of a Novel Stage of Beta-Herpesvirus Latency in Human Herpesvirus 6., J Virol. 77: 2258-2264, 2003

Non-patent Literature 5: Kondo Kazuhiro, "Herpes viruses kansen to hiroh (Infection with herpes viruses and fatigue)", Virus, Vol. 55 No. 1, pp. 9-18, 2005.

SUMMARY OF INVENTION

Technical Problem

Some of the present inventors identified a novel gene expressed in the intermediate stage in which specific genes to latent infection with HHV-6 are actively expressed and a novel small protein encoded by the intermediate transcript of HHV-6 (SITH-1). Through functional analysis of these genes and the protein SITH-1 encoded by the genes, the inventors have found new facts, that is, (i) the SITH-1 protein has a function that increases the concentration of the intracellular calcium, and (ii) an antibody against the SITH-1 protein is significantly detected from patients with mood disorder while it is not substantially detected from healthy subjects, and applied for patents (PCT/JP2008/67300).

As described above, detection of an antibody against the SITH-1 protein contained in biological samples from humans can be used for diagnosis of mental disorder and other diseases.

The serum antibody titer against the SITH-1 protein was determined by a conventional fluorescent antibody technique using 293T cells as antigens in which SITH-1 proteins are expressed. The inventors have continued the study and have discovered that the fluorescent antibody technique requires cumbersome processes such as fabrication of mammalian cells in which SITH-1 is expressed and production of preparation; the detection operation needs skill due to a low antibody titer in the human serum against the SITH-1 protein; and the SITH-1 protein requires careful handling due to its instability. Furthermore, the fluorescent antibody technique, which involves visual observation of fluorescence under the microscope after the reaction with a blood sample, is cumbersome and thus is unsuitable for simultaneous measurement of a large number of samples. In addition, some blood samples cannot be often measured due to nonspecific binding.

In view of such new knowledge by the inventors, an object of the present invention is to provide a simple and easy method for qualitatively and/or quantitatively detecting an antibody against a SITH-1 protein in a biological sample.

A particular object of the present invention is to provide a simple and easy method for qualitatively and/or quantitatively detecting and determining an antibody against a SITH-1 protein in a biological sample under a suppressed background signal level.

Solution to Problem

The inventors have discovered that a system of a SITH-1 protein bound to a carrier is useful for detection of antibodies and have conceived the present invention.

In particular, in order to detect a trace amount of SITH-1 protein in a biological sample in this system, counter measure was employed to reduce the background signal level. More specifically, nonspecific binding was reduced by addition of a cell homogenate extract to a biological sample. In a system of a SITH-1 protein immobilized on a carrier through binding between biotin and a biotin-binding protein, addition of a biotin binding protein as well as a cell homogenate extract to a biological sample exhibited a further outstanding reduction in nonspecific binding. Instead of addition of the biotin binding protein, substantially the same effect was achieved from addition of a cell homogenate extract prepared from cells genetically engineered to express a biotin-binding protein.

Based on the knowledge described above, the present invention provides a high-sensitive method for detecting an antibody against a SITH-1 protein with a reduced amount of nonspecific binding in a system of a SITH-1 protein immobilized on a carrier.

The present invention includes the following nonlimiting embodiments.

[Embodiment 1]

A method for detecting an antibody against a small protein encoded by the intermediate stage transcript of HHV-6 (SITH-1) in a biological sample, which comprises:

1) providing the SITH-1 protein;
2) binding the SITH-1 protein provided in step 1) to a carrier;
3) contacting the biological sample with the SITH-1 protein-bound carrier provided in step 2) to detect the SITH-1 protein antibody.

[Embodiment 2]

The method according to Embodiment 1, wherein the SITH-1 protein is selected from the group consisting of:

(a) a protein which has an amino acid sequence of SEQ ID NO: 1;
(b) a protein which has an amino acid sequence comprising deletion, substitution, insertion, and/or addition of one or more amino acids in the amino acid sequence of SEQ ID NO: 1 and which has the ability to increase the intracellular calcium concentration;
(c) a protein which has an amino acid sequence sharing an identity of at least 80% with the amino acid sequence of SEQ ID NO: 1 and which has the ability to increase the intracellular calcium concentration;
(d) a protein which has an amino acid sequence encoded by a nucleic acid consisting of the nucleotide sequence of SEQ ID NO: 2;
(e) a protein which has an amino acid sequence encoded by a nucleic acid consisting of a nucleotide sequence comprising deletion, substitution, insertion and/or addition of one or more nucleotides in the nucleotide sequence of SEQ ID NO: 2 and which has the ability to increase the intracellular calcium concentration;
(f) a protein which has an amino acid sequence encoded by a nucleic acid consisting of a nucleotide sequence sharing an identity of 80% or more with the nucleotide sequence of SEQ ID NO: 2 and which has the ability to increase the intracellular calcium concentration; and
(g) a protein which is encoded by a nucleic acid hybridizable under stringent hybridization conditions with a nucleic acid consisting of a nucleotide sequence complementary to the nucleotide sequence of SEQ ID NO: 2 and which has the ability to increase the intracellular calcium concentration.

[Embodiment 3]

The method according to Embodiment 1 or 2, wherein step 3) in Embodiment 1 comprises adding a mixture of:

(a) the biological sample, and
(b) a cell homogenate extract prepared from cells of the same species as that of host cells used to express the SITH-1 protein in step 1) to the SITH-1 protein-bound carrier prepared in step 2).

[Embodiment 4]

The method according to any one of Embodiments 1 to 3, wherein step 2) in Embodiment 1 comprising binding the SITH-1 protein to the carrier through binding between biotin and a biotin-binding protein.

[Embodiment 5]

The method according to Embodiment 4, wherein step 3) in Embodiment 1 comprises adding a mixture of:

(a) the biological sample, and
(b-i) a cell homogenate extract prepared from cells of the same species as that of host cells used to express the SITH-1 protein, a biotinylated SITH-1 protein and/or a biotin-binding protein in step 1) or 2), in combination with a biotin-binding protein; or
(b-ii) a cell homogenate extract prepared from cells genetically engineered to express a biotin-binding protein, wherein the cells are of the same species as that of host cells used to express the SITH-1 protein, a biotinylated SITH-1 protein and/or a biotin-binding protein in step 1) or 2) to the SITH-1 protein-bound carrier prepared in step 2).

[Embodiment 6]

The method according to any one of Embodiments 3 to 5, wherein, step 3(b) in Embodiment 3 or step 3(b-i) in Embodiment 5 comprises adding, as the cell homogenate extract, a cell homogenate extract extracted from cells comprising any vector.

[Embodiment 7]

The method according to any one of Embodiments 4 to 6, wherein the biotin-binding protein is tamavidin or a mutant thereof.

[Embodiment 8]

The method according to any one of Embodiments 1 to 7, wherein the biological sample is selected from the group consisting of blood, serum, cerebrospinal fluid, saliva, throat swab, sweat, urine, tear, lymph, semen, peritoneal fluid, and mother's milk.

[Embodiment 9]

A carrier for detecting an antibody against a small protein encoded by the intermediate stage transcript of HHV-6 (SITH-1) in a biological sample, wherein the carrier comprises the SITH-1 protein bound thereto.

[Embodiment 10]

The carrier according to Embodiment 9, wherein the SITH-1 protein and the carrier are bound to each other through binding between biotin and a biotin-binding protein.

[Embodiment 11]

A kit for detecting an antibody against a small protein encoded by the intermediate stage transcript of HHV-6 (SITH-1) in a biological sample, which comprises:

A) a carrier comprising the SITH-1 protein bound thereto; and

B) an agent for diluting the biological sample, which comprises a cell homogenate extract prepared from cells of the same species as that of host cells used to express the SITH-1 protein in A).

[Embodiment 12]

The kit according to Embodiment 11, wherein the carrier in A) is a carrier comprising the SITH-1 protein bound thereto through binding between biotin and a biotin-binding protein, and wherein the agent in B) is an agent for diluting the biological sample, which comprises:

i) a cell homogenate extract prepared from cells of the same species as that of host cells used to express the SITH-1 protein, a biotinylated SITH-1 protein and/or a biotin-binding protein, in combination with a biotin-binding protein in A); or ii) a cell homogenate extract prepared from cells genetically engineered to express a biotin-binding protein, wherein the cells are of the same species as that of host cells used to express the SITH-1 protein, the biotinylated SITH-1 protein and/or the biotin-binding protein in A).

[Embodiment 13]

A kit for detecting an antibody against a small protein encoded by the intermediate stage transcript of HHV-6 (SITH-1) in a biological sample, which comprises:

A) the SITH-1 protein;

B) a carrier for immobilizing the SITH-1 protein in A); and

C) an agent for diluting a biological sample, which comprises a cell homogenate extract prepared from cells of the same species as that of host cells used to express the SITH-1 protein in A).

[Embodiment 14]

The kit according to Embodiment 13, wherein the SITH-1 protein in A) is biotinylated, wherein the carrier in B) is directly or indirectly bound to a biotin-binding protein, and wherein the agent in C) is an agent for diluting the biological sample, which comprises:

i) a cell homogenate extract prepared from cells of the same species as that of host cells used to express the SITH-1 protein, a biotinylated SITH-1 protein and/or a biotin binding protein, in combination with a biotin-binding protein in A) or B); or ii) a cell homogenate extract prepared from cells genetically engineered to express a biotin-binding protein, wherein the cells are of the same species as that of host cells used to express the SITH-1 protein, the biotinylated SITH-1 protein and/or the biotin-binding protein in A) or B).

Advantageous Effects of Invention

The method of the present invention enables high-sensitivity and stable detection, with a reduced background signal level, of an SITH-1 protein antibody in a biological sample. In particular, the method of the present invention enables detection and determination of an SITH-1 protein antibody which is present in a trace amount in a biological sample and cannot be readily detected by conventional methods.

BRIEF DESCRIPTION OF DRAWINGS

FIG. 1A illustrates the result of Western blotting for the detection of the SITH-1 protein; and FIG. 1B illustrates the result of activity staining for the detection of a biotinylated protein.

*E. coli* BL21 (DE3) expressing a BioEase tagged fusion SITH-1 protein was sonicated, and the resulting crude *E. coli* extract fraction was developed onto SDS-PAGE (15% acrylamide gel) so as to give 20 μg total protein/lane, and then was transferred onto a PVDF film.

Figure 1:
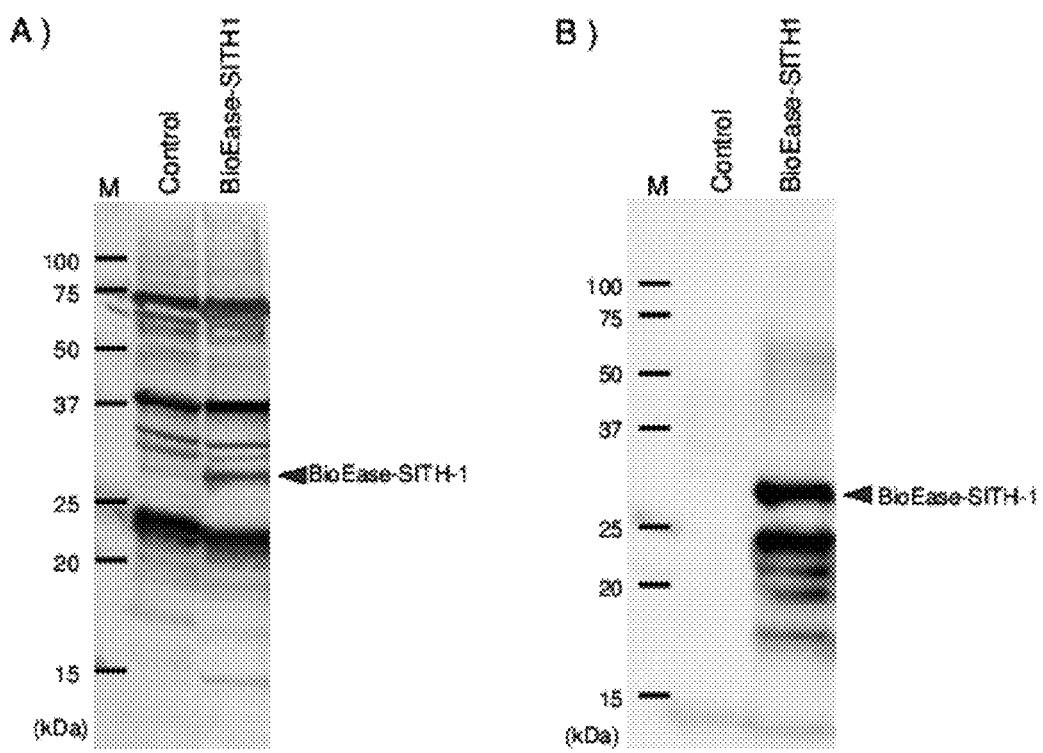
FIG. 1 illustrates expression of a BioEase tagged (biotin tagged) fusion SITH-1 protein.

In further detail, in FIG. 1A, after the reaction of an anti-SITH-1 antibody (1/1000 dilution), alkaline phosphatase (AP) labeled anti-rabbit IgG antibody (1/1000 dilution) was reacted followed by AP staining. FIG. 1B is a stained image after the reaction of streptavidin-horseradish peroxidase (HRP) (1/1000 dilution). In FIGS. 1A and 1B, "Control" represents an extract sample derived from *E. coli* having only an expression vector. The arrow indicates the position of the BioEase tagged fusion SITH-1 protein.

The Streptavidin-HRP staining chromatogram in FIG. 1B shows two broad bands. The lower band, which is not detected in the anti-SITH-1 antibody chromatogram in FIG. 1A, seems to be a BioEase tagged protein of which part of the SITH-1 site is decomposed.

Figure 2:
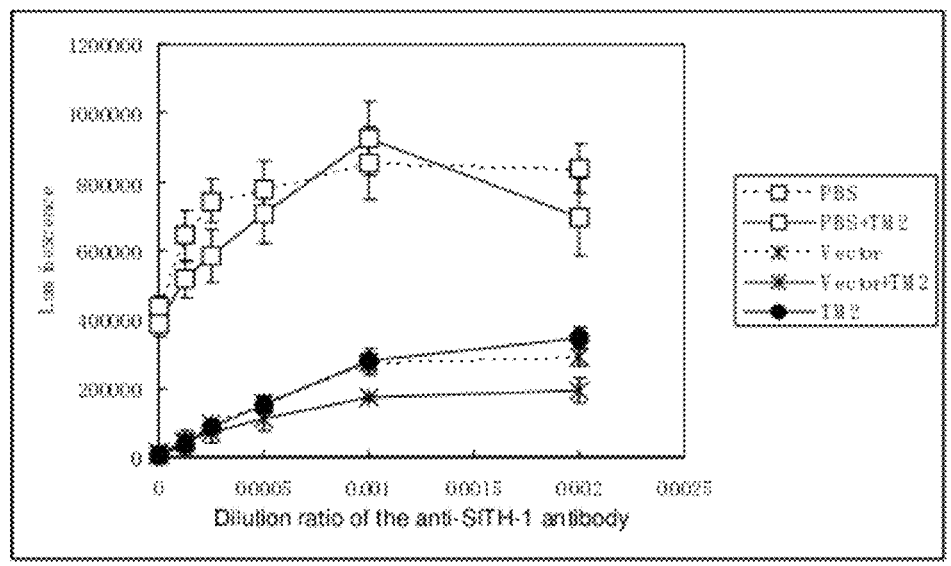

FIG. 2 is a graph illustrating the effect of various diluents for sera on nonspecific binding. Open squares tied by broken lines indicate a sample of the serum diluted in PBS; Open squares tied by solid lines indicates a sample diluted in PBS containing purified tamavidin 2 (TM2); Asterisks tied by broken lines indicate a sample diluted in a broken *E. coli* extract having only an expression vector; Asterisks tied by solid line indicate a sample diluted in a broken *E. coli* extract having only an expression vector and containing purified TM2; and Closed circles tied by solid lines indicate a sample diluted in a TM2 expressing broken *E. coli* extract. The longitudinal axis (luminescence) of each graph represents the amount of the detected anti-SITH-1 antibody while the lateral axis represents the dilution ratio of the anti-SITH-1 antibody which is gradually diluted.

Figure 3:
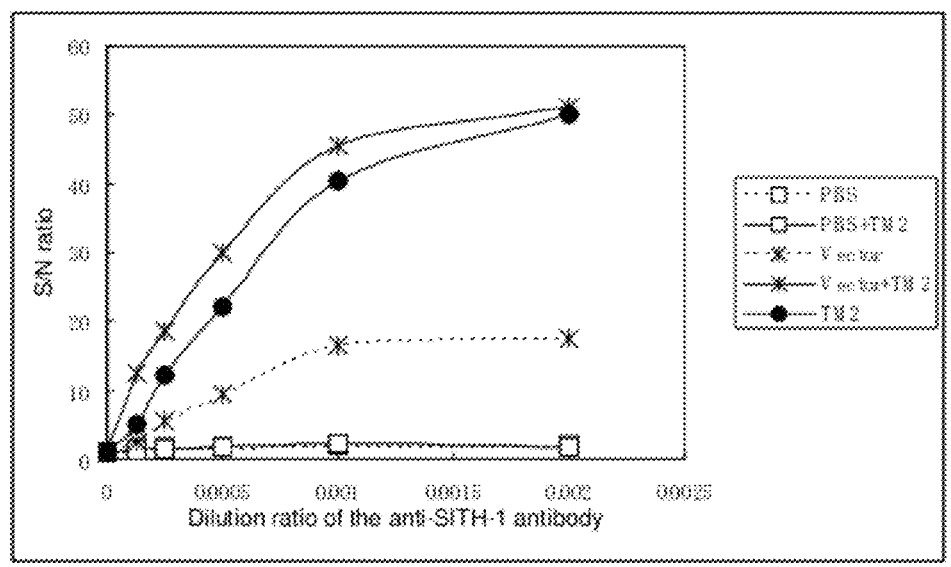

FIG. 3 is a graph of the S/N ratio at various dilution ratios of the anti-SITH-1 antibody, the ratio being calculated from the results shown in FIG. 2.

Open squares tied by broken lines indicate a sample of the serum diluted in PBS; Open squares tied by solid lines indicates a sample diluted in PBS containing purified tamavidin 2 (TM2); Asterisks tied by broken lines indicate a sample diluted in a broken *E. coli* extract having only an expression vector; Asterisks tied by solid line indicate a sample diluted in a broken *E. coli* extract having only an expression vector and containing purified TM2; and Closed circles tied by solid lines indicate a sample diluted in a TM2 expressing broken *E. coli* extract.

Figure 4:
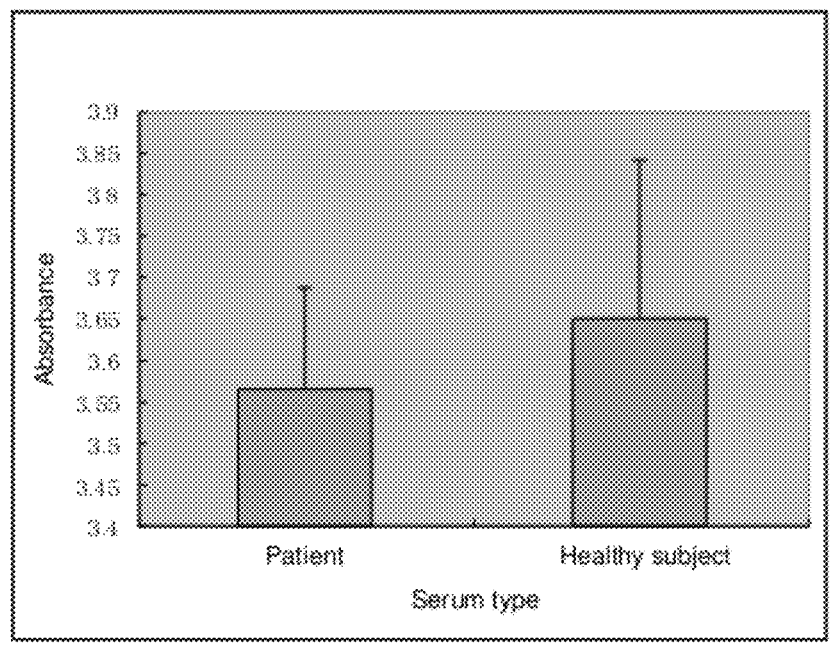

FIG. 4 is a graph illustrating the observed anti-SITH-1 antibody titer in human sera in the case of the use of a TM2 plate with a biotinylated SITH-1 bound thereto. A solution of each human serum diluted in a TBS-T (tris-buffered saline, 0.1% Tween 20) containing 1% casein was exposed to the TM2 plate.

Figure 5:
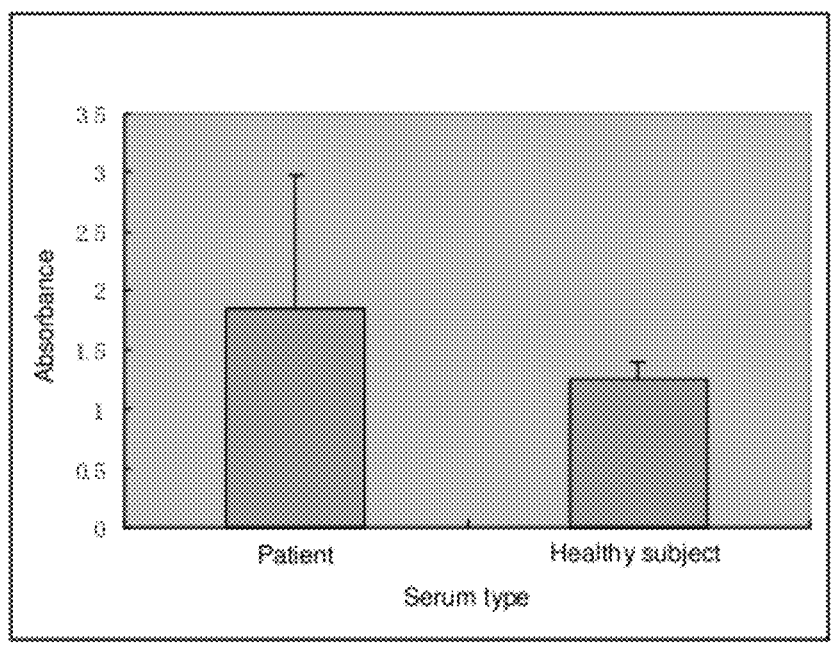

FIG. 5 is a graph illustrating the observed anti-SITH-1 antibody titer in human sera in the case of the use of a TM2 plate comprising a biotinylated SITH-1 bound thereto. A solution of each human serum diluted in a crude *E. coli* extract was exposed to the TM2 plate.

Figure 6:
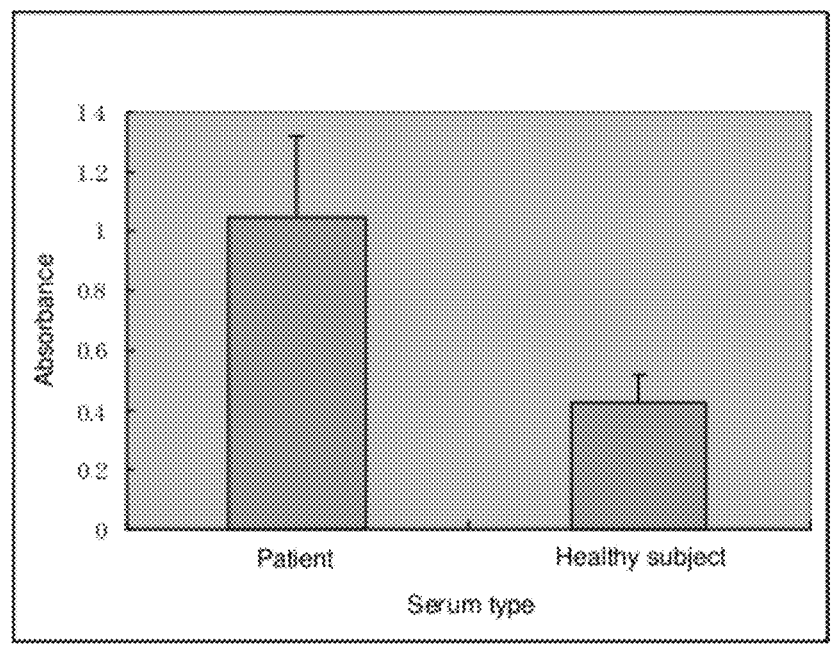

FIG. 6 is a graph illustrating the observed anti-SITH-1 antibody titer in human sera in the case of the use of a TM2 plate comprising a biotinylated SITH-1 bound thereto. A solution of each human serum diluted in a TM2 expressing *E. coli* extract containing 5 mg total protein/ml was exposed to the TM2 plate.

Figure 7:
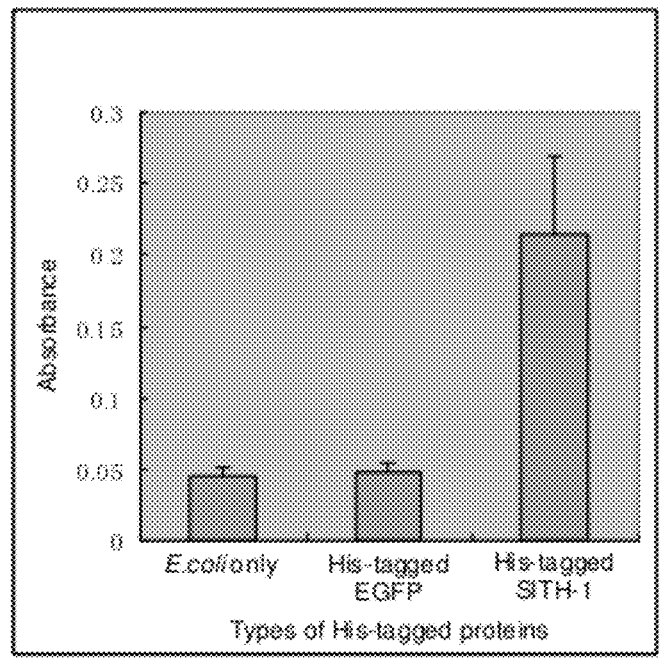

FIG. 7 is a graph illustrating the observed anti-SITH-1 antibody titer in an anti-SITH-1 rabbit serum in the case of the use of a nickel plate comprising a His-tagged fusion SITH-1 protein bound thereto. A solution of the anti-SITH-1 rabbit serum 100-fold diluted in PBS(−) containing 0.2% BSA was added. Non-expressing *E. coli* and His-tagged EGFP were used as controls.

Figure 8:
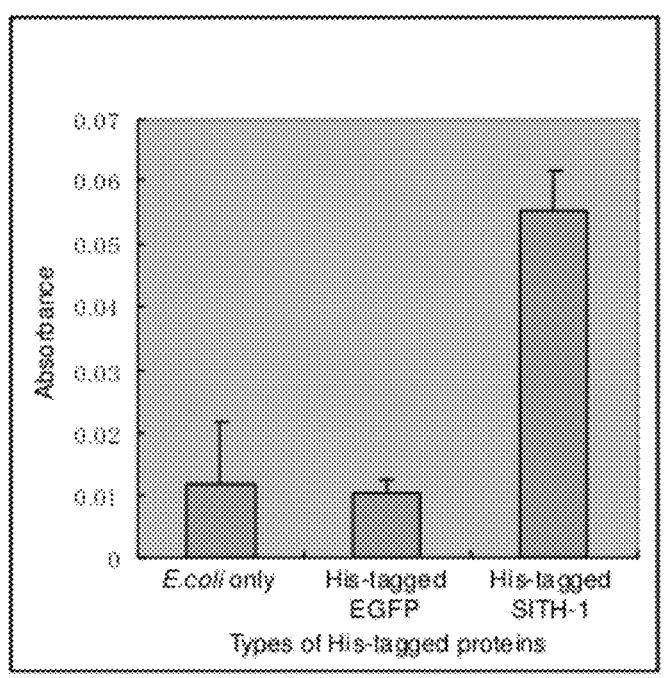

FIG. 8 is a graph illustrating the observed anti-SITH-1 antibody titer in an anti-SITH-1 rabbit serum in the case of the use of a nickel plate comprising a His-tagged fusion SITH-1 protein bound thereto. A solution of the anti-SITH-1 rabbit serum 500-fold diluted in PBS(−) containing 0.2% BSA was added. Non-expressing *E. coli* and His-tagged EGFP were used as controls.

Figure 9:
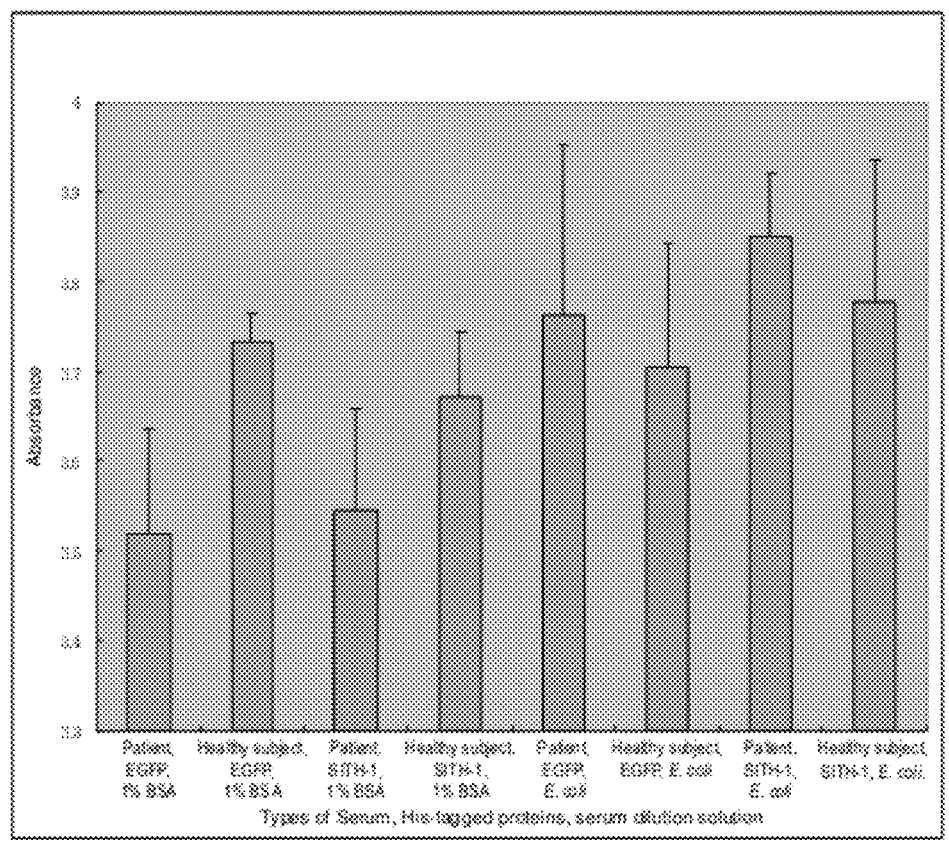

FIG. 9 is a graph illustrating the observed anti-SITH-1 antibody titer in human sera in the case of the use of a nickel plate comprising a His-tagged fusion SITH-1 protein bound thereto. A 100-fold diluted solution of each human serum was added. His-tagged EGFP was used as a control. The serum dilution solution used was 1% BSA or a crude *E. coli* extract.

Figure 10:
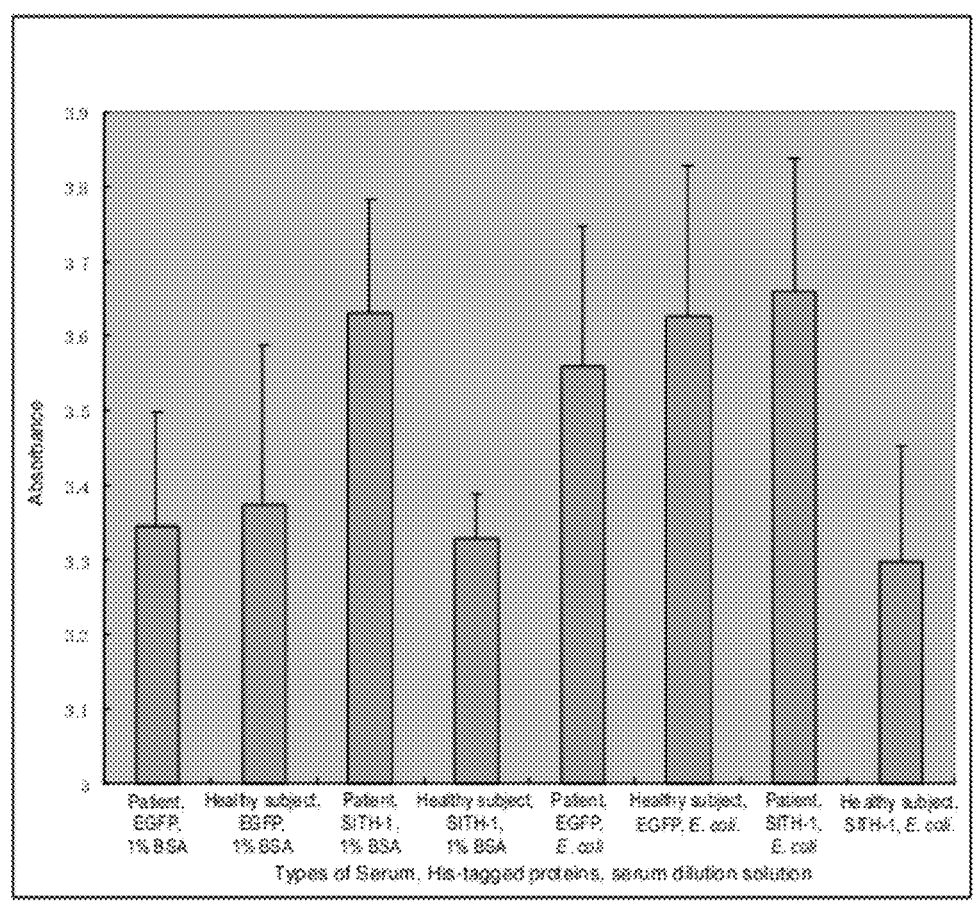

FIG. 10 is a graph illustrating the observed anti-SITH-1 antibody titer in human sera in the case of the use of a nickel plate comprising a His-tagged fusion SITH-1 protein bound thereto. A 500-fold diluted solution of each human serum was added. His-tagged EGFP was used as a control. The serum dilution solution used was 1% BSA or a crude *E. coli* extract.

EMBODIMENTS OF INVENTION

I. Method for Detecting Antibody Against SITH-1 in Biological Sample

The present invention provides a method for detecting an antibody against a small protein encoded by the intermediate stage transcript of HHV-6 (SITH-1) in a biological sample.

The method of detection according to the present invention includes:

1) providing a SITH-1 protein;

2) binding the SITH-1 protein prepared in step 1) to a carrier;

3) contacting a biological sample with the SITH-1 protein-bound carrier provided in step 2) to detect the SITH-1 protein antibody.

1. Biological Sample

The present invention relates to a method for detecting an antibody against a SITH-1 protein in a biological sample The biological samples usable in the present invention are derived from humans, laboratory animals infected with HHV-6 or laboratory animals introduced with SITH-1 gene, and contain a SITH-1 protein antibody to be detected. Such samples can be used without limitation. Examples of the sample include cells collected from humans, laboratory animals infected with HHV-6 such as monkey, or laboratory animals introduced with SITH-1 gene such as mouse, samples containing tissues or fragments thereof, for example, humor, preferably, blood, serum, cerebrospinal fluid, saliva, throat swab, sweat, urine, tear, lymph fluid, semen, peritoneal fluid, and mother's milk.

These humors may be used after dilution as needed. The dilution ratio is, but not limited to, generally in the range of about 10 to about 10000 fold, preferably about 100 to 1000 fold. The diluent may be any buffer solution, which may contain any proper blocking agent. Preferred blocking agents have high inhibitory effect on nonspecific binding, and can be selected from well known blocking agents to persons skilled in the art, such as BSA and casein.

The method of the present invention enables detection and accurate quantitative determination of the SITH-1 protein antibody from, for example, samples which are derived from patients with autoimmune disorders and contain a large amount of nonspecific binding precluding detection of the target antibody in conventional methods, or samples which are derived from healthy subjects and have high background levels caused by, for example, autologous antibodies. The SITH-1 protein antibody, which exhibits a low antibody titer, requires suppression of dilution ratio of the serum. As a result, nonspecific binding derived from serum components inevitably increases. Thus, no known method enables detection or determination of quantity for the antibody. In contrast, the method of the present invention can readily detect and accurately determine quantity of the antibody.

2. SITH-1 Protein

The SITH-1 protein in the present invention refers to a small protein encoded by the intermediate transcript of HHV-6 and mutants thereof.

SITH-1 Based on Description in PCT/JP2008/67300

(1) SITH-1 Protein and Nucleic Acid

The structures and functions of the SITH-1 protein and a nucleic acid are disclosed in PCT/JP2008/67300, and the entity thereof is incorporated therein.

The SITH-1 is a factor involving latent infection with herpes viruses, and more particularly, a protein specifically expressed during latent infection with herpes viruses. The term "specifically expressed during latent infection with herpes viruses" therein refers to specific expression of genes or gene products derived from herpes viruses during latent infection (not productive infection) with herpes viruses in hosts infected with herpes viruses.

The SITH-1 protein is preferably selected from the group consisting of:

(a) a protein which has an amino acid sequence of SEQ ID NO: 1;

(b) a protein which has an amino acid sequence comprising deletion, substitution, insertion, and/or addition of one or more amino acids in the amino acid sequence of SEQ ID NO: 1 and which has the ability to increase the intracellular calcium concentration;

(c) a protein which has an amino acid sequence sharing an identity of at least 80% with the amino acid sequence of SEQ ID NO: 1 and which has the ability to increase the intracellular calcium concentration;

(d) a protein which has an amino acid sequence encoded by a nucleic acid consisting of the nucleotide sequence of SEQ ID NO: 2;

(e) a protein which has an amino acid sequence encoded by a nucleic acid consisting of a nucleotide sequence comprising deletion, substitution, insertion and/or addition of one or more nucleotides in the nucleotide sequence of SEQ ID NO: 2 and which has the ability to increase the intracellular calcium concentration;

(f) a protein which has an amino acid sequence encoded by a nucleic acid consisting of a nucleotide sequence sharing an identity of 80% or more with the nucleotide sequence of SEQ ID NO: 2 and which has the ability to increase the intracellular calcium concentration; and (g) a protein which is encoded by a nucleic acid hybridizable under stringent hybridization conditions with a nucleic acid consisting of a nucleotide sequence complementary to the nucleotide sequence of SEQ ID NO: 2 and which has the ability to increase the intracellular calcium concentration.

The SITH-1 protein typically has an amino acid sequence of SEQ ID NO: 1. The amino acid sequence of SEQ ID NO: 1 is preferably encoded by a nucleic acid consisting of the nucleotide sequence of SEQ ID NO: 2.

The SITH-1 protein having the amino acid sequence of SEQ ID NO: 1, as described in Reference Example below, was isolated and identified as a protein which is specifically expressed during latent infection with human herpes viruses 6 (HHV-6). The SITH-1 protein is a protein having the amino acid sequence of SEQ ID NO: 2, composed of 159 amino acids, and having a molecular mass of about 17.5 kDa.

The SITH-1 protein is encoded by the nucleic acid of the SITH-1 gene. The cDNA of this SITH-1 gene, as shown in SEQ ID NO: 3, has a size of 1795 base pairs (about 1.79 kbp), the nucleotide sequence from the 954-th to 956-th being the initiation codon (Kozak ATG), while the nucleotide sequence from 1431-st to 1433-rd being the termination codon (TAA). Accordingly, the SITH-1 nucleic acid has a nucleotide sequence from 954-th to 1430-th as an open reading frame (ORF) among the nucleotide sequence of SEQ ID NO: 3, the ORF having a size of 477 base pairs (about 0.48 kbp). Among the cDNA of the SITH-1, the nucleotide sequence representing the ORF region is shown in SEQ ID NO:2. The nucleotide sequence of SEQ ID NO: 2 includes three bases of the stop codon.

The SITH-1 nucleic acid is always expressed in the cytoplasm of a cell latent-infected with HHV-6, but not in a productively infected cell. The nucleic acid encoding the SITH-1 protein is encoded by a DNA which is a complementary strand of the HHV-6 latent infection specific gene (H6LT), which has been reported to date, and its expression is enhanced in the intermediate stage of the latent infection with HHV-6. These facts demonstrate that the SITH-1 protein is a protein which is specifically expressed during latent infection with HHV-6.

The SITH-1 protein binds to a host protein, CAML (calcium-modulating cyclophilin ligand, Accession #; U18242) to increase the calcium concentration in the glial cells. The CAML is a protein which is known to be abundantly present in the brain and lymphocyte in the host living organism and increase the intracellular calcium concentration. Probably, an increase in intracellular calcium concentration due to expression of the SITH-1 protein leads to activation of overall signaling in the latent-infected cells, and thus contributes to effective reactivation of HHV-6.

It is known that the glial cells in the brain are latent-infected with HHV-6. When HHV-6 during the latent infection or at the intermediate stage which is a latent infection state with high activity expresses the SITH-1, the calcium concentration seems to increase in the glial cells. It is believed that an increase in intracellular calcium concentration in the brain is wedded to psychiatric disorders uch as mood disorders (Riken Annual Report 2003).

The SITH-1 protein has a function that maintains activity to bind to the host protein, CAML to increase the intracellular calcium concentration. Furthermore, expression of the SITH-1 protein in the glial cells (in which this protein seems to be most strongly expressed) in the brain can induce psychiatric disorders. Accordingly, the SITH-1 protein is believed to be expressed during the latent infection with herpes viruses or at the initial stage of reactivation of the herpes viruses to cause the host to have any psychiatric disorder.

(b) An exemplary mutant of the SITH-1 protein may be a protein which has an amino acid sequence comprising deletion, substitution, insertion, and/or addition of one or more amino acids in the amino acid sequence of SEQ ID NO: 1 and which has the ability to increase the intracellular calcium concentration, like the SITH-1 protein.

More particularly, the protein has an amino acid sequence comprising deletion, substitution, insertion, and/or addition of one or more amino acids (preferably one or several amino acids, e.g., 1 to 40, 1 to 30, 1 to 20, 1 to 15, more preferably 10, 9, 8, 7, 6, 5, 4, 3, 2 or 1 amino acid) in the amino acid sequence of SEQ ID NO: 1, and has the aforementioned ability of the present invention. The term "an amino acid sequence comprising deletion, substitution, insertion, and/or addition" herein refers to the presence of deletion, substitution, insertion, and/or addition at any one or more sites in the same amino acid sequence. Although two or more of the deletion, substitution, insertion, and addition may occur at the same time, it is generally preferred that the number of deletions, substitutions, insertions, and additions are as small as possible.

The substitution described above is preferably conservative substitution. The conservative substitution refers to replacement of a specific amino acid residue with any residue having similar physicochemical features. Any substituent may be employed that the feature on the structure of the original sequence is not substantially varied. Nonlimiting examples of the conservative substitution include substitutions between amino acid residues containing aliphatic groups, such as mutual substitution between Ile, Val, Leu, and Ala; and substitutions between polar residues, such as mutual substitution between Lys and Arg, between Glu and Asp, and between Gln and Asn.

In the non-conservative substitution, any one member of these types may be replaced with one of the other members, preferably in view of the hydropathic index of the amino acid (hydropathic amino acid index) (Kyte et al, J. Mol. Biol., 157:105-131 (1982)) in order to maintain the biological function of the protein of the present invention. In the non-conservative substitution, amino acids may be replaced based on hydrophilicity.

The protein having an amino acid sequence comprising deletion, substitution, insertion, or addition of one or more amino acids in the amino acid sequence of SEQ ID NO: 1 can be prepared by a technique such as site-specific mutagenesis described in, for example, "Molecular Cloning, A Laboratory Manual 3rd ed." (Cold Spring Harbor Press (2001)). The term "one or more amino acids" herein refers to amino acid which can be deleted, substituted, inserted, and/or added by site-specific mutagenesis.

Examples of the techniques, other than the site-specific mutagenesis, of introducing the deletion, substitution, or addition of one or more amino acids into the amino acid sequence of the protein while its ability is maintained include treatment of the gene in a mutagen and linking after deletion, substitution, or addition of a nucleotide which is selected by selective cleavage of the gene.

(c) Another mutant of the SITH-1 protein of the present invention may be a protein which has an amino acid sequence sharing an identity of at least 80% with the amino acid sequence of SEQ ID NO: 1 and which has the ability to increase the intracellular calcium concentration.

The identity of the amino acid sequence is preferably at least 85%, 90%, 95%, 96%, 97%, 98%, or 99%, more preferably 99.3%.

The percent identity between two amino acid sequences can be determined by visual inspection and mathematical calculation. Alternatively, the percent identity between two protein sequences can be determined through comparison of sequence information using a GAP computer program available from the University of Wisconsin Genetics Computer Group (UWGCG) based on the algorithm by Needleman, S. B. and Wunsch, C. D. (J. Mol. Biol., 48: 443-453, 1970). Preferred default parameters of the GAP program include: (1) scoring matrix: blosum62 described in Henikoff, S, and Henikoff, J. G. (Proc. Natl. Acad. Sci. USA, 89: 10915-10919, 1992); (2) 12 gap weights; (3) 4 gap length weights; and (4) no penalty for terminal gaps.

Any other program used by persons skilled in the art can also be used for comparison of the sequences. The percent identity can be determined by, for example, comparison with the sequence information using a BLAST program described in Altschul et. al., (Nucl. Acids. Res., 25, p. 3389-3402, 1997). This program can be available from the websites of National Center for Biotechnology Information (NCBI) or DNA Data Bank of Japan (DDBJ) on the Internet. The conditions (parameters) for identity search by the BLAST program is described in detail on these sites. Although these parameters can be partly modified if necessary, search is generally carried out using the default values. Alternatively, the percent identity between two amino acid sequences may be determined using a program such as genetic information processing software GENETYX Ver. 7 (available from GENETYX CORPORATION) or FASTA algorithm, wherein search may be carried out using the default values.

(e) Another mutant of the SITH-1 protein of the present invention may be a protein which has an amino acid sequence encoded by a nucleic acid consisting of a nucleotide sequence comprising deletion, substitution, insertion and/or addition of one or more nucleotides in the nucleotide sequence of SEQ ID NO: 2 and which has the ability to increase the intracellular calcium concentration.

More particularly, a nucleic acid which has a nucleotide sequence comprising deletion, substitution, insertion, and/or addition of one or more nucleotides (preferably one or several nucleotides, e.g., 1 to 120, 1 to 90, 1 to 60, 1 to 30, 1 to 20, 1 to 15, more preferably 10, 9, 8, 7, 6, 5, 4, 3, 2, or 1 nucleotide) in the nucleotide sequence of SEQ ID NO: 2, and which has nucleotide sequence encoding the protein having the aforementioned ability of the present invention. The term "nucleotide sequence comprising deletion, substitution, insertion, and/or addition of one or more nucleotides" herein refers to the presence of deletion, substitution, and/or addition at any one or more sites in the same nucleotide sequence. Although two or more of the deletions, substitutions, insertions, and additions may occur at the same time, it is generally preferred that the number of deletions, substitutions, insertions, and additions be as small as possible.

(f) Another mutant of the SITH-1 protein of the present invention may be a protein which has an amino acid sequence encoded by a nucleic acid consisting of a nucleotide sequence sharing an identity of 80% or more with the nucleotide sequence of SEQ ID NO: 2 and which has the ability to increase the intracellular calcium concentration.

The identity of the nucleotide sequence is preferably at least 85%, 90%, 95%, 96%, 97%, 98%, or 99%, more preferably 99.3%.

The percent identity between two nucleotide sequences can be determined by visual inspection and mathematical calculation. Preferably, such comparison can be carried out through comparison of sequence information using a computer program. A particularly preferred computer program is a version 10.0 program "GAP", Wisconsin package of Genetics Computer Group (GCG, Madison, Wis.) (Devereux, et al., 1984, Nucl. Acids Res., 12: 387). The use of the "GAP" program enables comparison between two amino acid sequences and comparison between a nucleotide sequence and an amino acid sequence, in addition to comparison of two nucleotide sequences.

(g) Another mutant of the SITH-1 protein may be a protein which is encoded by a nucleic acid hybridizable under stringent hybridization conditions with a nucleic acid consisting of a nucleotide sequence complementary to the nucleotide sequence of SEQ ID NO: 2 and which has the ability to increase the intracellular calcium concentration.

The stringency of hybridization conditions are primarily determined by the hybridization conditions itself, more preferably by the hybridization conditions and washing conditions. The term "stringent conditions" includes moderately or highly stringent conditions.

More particularly, examples of moderately stringent conditions include hybridization conditions of 1×SSC to 6×SSC at 42° C. to 55° C., more preferably 1×SSC to 3×SSC at 45° C. to 50° C., most preferably 2×SSC at 50° C. In the case of a hybridization solution containing about 50% formamide, a temperature which is 5 to 15° C. lower than the aforementioned temperature is employed. Examples of washing condition include 0.5×SSC to 6×SSC at 40° C. to 60° C. For hybridization and washing, generally 0.05% to 0.2%, preferably about 0.1% SDS may be added.

Highly stringent (high stringent) conditions involve hybridization and/or washing at a higher temperature and/or a lower salt content than the moderately stringent conditions. Examples of hybridization conditions include 0.1×SSC to 2×SSC at 55° C. to 65° C., more preferably 0.1×SSC to 1×SSC at 60° C. to 65° C., most preferably 0.2×SSC at 63° C. Examples of washing conditions include 0.2×SSC to 2×SSC at 50° C. to 68° C., more preferably 0.2×SSC at 60 to 65° C.

A nonlimiting example of the hybridization condition is as follows: prehybridization is carried out in 5×SSC, 1% SDS, 50-mM Tris-HCl (pH 7.5) and 50% formamide at 42° C., a probe is added, the system is maintained at 42° C. overnight to form hybrid, and then the sample is washed three times in 0.2×SSC and 0.1% SDS at 65° C. for 20 minutes.

(2) Antibody Against SITH-1

The antibody against the SITH-1 can be prepared as a polyclonal antibody or a monoclonal antibody from the SITH-1 protein, its mutant, or their partial peptides as antigen by a known process. Examples of the known process are described in documents such as Harlow et al. "Antibodies: A laboratory manual (Cold Spring Harbor Laboratory, New York (1988))" and Iwasaki et. al. "Monoclonal Antibody: Hybridoma and ELISA, Kodansha (1991)". The resulting antibody can be used for detection and determination of the SITH-1 protein.

The term "antibody" refers to immunoglobulins (IgA, IgD, IgE, IgG, IgM, and Fab fragment, F(ab')$_2$ fragment, and Fc fragment thereof). Examples of the immunoglobulins include, but not limited to, polyclonal antibodies, monoclonal antibodies, single-stranded antibodies, antiidiotype antibodies, and humanized antibodies.

The term "antibody recognizing the SITH-1 protein" includes complete molecules and antibody fragments specifically attachable to the SITH-1 protein (for example, Fab and F(ab')$_2$ fragment). Fab, F(ab')$_2$, and other fragments of the SITH-1 antibody can be used according to the method disclosed in the present specification or any known method. Such fragments can be typically produced by cleavage by proteolysis using an enzyme e.g., papain (yielding a Fab fragment) or pepsin (yielding a F(ab')$_2$ fragment).

It is believed that patients having mood disorders and individuals having potential mood disorders exhibit increased expression levels of the SITH-1 protein and thus increased SITH-1 antibody titers. In one embodiment of the present invention, detection of the SITH-1 antibody in a biological sample enables identification of patients having mood disorders and individuals having potential mood disorders.

3. SITH-1 Protein-Bound Carrier

The method of the present invention includes:
1) providing the SITH-1 protein;
2) binding the SITH-1 protein provided in step 1) to a carrier; and uses the SITH-1 protein-bound carrier.

Providing SITH-1 Protein

The SITH-1 protein for detecting the SITH-1 antibody can be provided by any known process for preparation of proteins. It can be prepared, for example, by the following nonlimiting procedures.

The SITH-1 protein can be expressed in a desired host cell by integration of a gene encoding the SITH-1 protein into an expression vector. Nonlimiting examples of host cells include mammalian cells (e.g., cells derived from primates, such as human and monkey; rodents such as mouse, rat, Chinese hamster, and canine), insect cells (expression systems utilizing baculovirus and *Drosophila* system), yeast, *E. coli*, plants, and *Bacillus subtilis*. Preferred is *E. coli*. In addition, established culture cell systems can be preferably used, for example, HEK293, HeLa, HepG2, and 293T for human cells; CHO, NIH3T3, and PC12 for rodent cells; COS-1, COS-7, MDCK, and Vero for other mammalian cells; and Sf9 and S2 for insect cells. Alternatively, the protein can be expressed using cell-free expression systems such as wheat germ extract and insect cell extract.

Persons skilled in the art can appropriately select expression vectors suitable for host cells used.

The expressed SITH-1 protein may be purified. In the case where it is immobilized on a carrier by a strong bond such as an avidin-biotin bond, a carrier comprising avidin or biotin bound thereto may be directly reacted with the SITH-1 protein expressing cell extract without preliminary purification; this process achieves purification and immobilization at the same time.

The SITH-1 protein can be purified by any method well known to persons skilled in the art, for example, a combination of chromatographic processes, such as ordinary ion-exchange chromatography, hydrophobic chromatography, and gel-permeation chromatography or use of a tag sequence for purification. In such a case, the SITH-1 protein may be expressed in any host cell such as *E. coli* cells and mammalian cells as fusion proteins with, for example, glutathione-S-transferase, maltose-binding proteins, cellulose-binding proteins, chitin-binding proteins, and thioredoxin-binding proteins, and the resulting proteins may be purified by affinity with glutathione, maltose, cellulose, chitin, and thioredoxin, respectively (for example, using a glutathione-fixed column).

Preliminary introduction of the recognition site of the protease into the fusion site with the SITH-1 protein enables removal of the tag sequence by treating the protease after purification. Any protease well known to persons skilled in the art such as enterokinase and Factor Xa can be used. Alternatively, the protein can be purified by a combination of HisTag, FlagTag, or Strep(II)-Tag with ionized nickel, anti-Flag antibody, or a Strep-Tactin column. In order to enhance the purity, multiple tags may be fused to the SITH-1 protein so that the protein is purified by a combined process. For example, the terminal of the SITH-1 protein may be fused with a biotinylated sequence such as HisTag and BioEASE™, expressed as a recombination protein in a host, purified through a nickel column, and then further purified through a low affinity avidin or low affinity streptavidin (e.g., SA mutein, Roche) column.

Carrier

Examples of materials for solid carrier include, but not limited to, cellulose, Teflon (registered trademark), nitrocellulose, agarose, highly cross-linked spherical agarose, dextran, chitosan, polystyrene, polyacrylamide, polyesters, polycarbonates, polyamides, polypropylene, nylons, polyvinylidene difluoride, latex, polystyrene latex, silica, glass, glass fiber, gold, platinum, silver, copper, iron, stainless steel, ferrite, silicon wafer, polyethylene, polyethyleneimine, poly(lactic acid), resin, polysaccharides, proteins such as albumin, carbon, and combination thereof. Preferred materials have a certain level of strength, a stable composition, and reduced nonspecific binding.

Examples of the form of the solid carrier include, but not limited to, microbeads, magnetic beads, thin films, capillary tubes, filters, plates, microplates, carbon nanotubes, and censor chips. Flat solid carriers such as thin films and plates may be provided with pits, grooves, or filter bottoms, as is known in the art.

In an embodiment of the invention, microbeads may have a spherical diameter in the range of about 25 nm to about 1 mm. In a preferred embodiment, the beads have a diameter in the range of about 50 nm to about 10 μm.

Without any limitation, for example, in the case that high sensitivity for detection is desired, beads as described above can preferably be used as the solid carrier in the view point that the beads provide high contacting frequency between the target substance to be detected and the substance which specifically binds to the target substance, and that cleaning operation thereof is easy.

Method for Binding SITH-1 Protein to Carrier

Binding SITH-1 Protein provided in Step 1) to carrier.

Binding the SITH-1 protein to the carrier may be carried out by any method for binding a protein to a carrier. Nonlimiting examples of such a method include use of hydrophobic bond, covalent bond, and various tags, and use of binding between biotin and a biotin-binding protein. In the case of the use of hydrophobic bond or covalent bond, preferably the SITH-1 protein is preliminarily purified.

In the case of the use of the hydrophobic bond, binding is achieved by interaction of the hydrophobic surface of a carrier with the hydrophobic moiety of the SITH-1 protein. For example, a SITH-1 protein solution is put into direct contact with a carrier surface such as a microplate (e.g., Nunc-Immuno™ Plate (Nunc), or SpectraPlate-96 HB(Perkin Elmer) or Reacti-Bind™ 96-Well Plates Corner Notch (PIERCE)), and is allowed to stand for a predetermined time, so that the SITH-1 protein is bound and immobilized on the carrier by the interaction of the hydrophobic moiety of the SITH-1 protein and the hydrophobic portion of the carrier.

On the other hand, in the case of the covalent bond, functional groups are provided on the surface of a carrier so as to be bound to the functional groups in the SITH-1 protein. For such binding, a variety of carriers provided with various surface functional groups are commercially available and can be preferably used in the invention. Nonlimiting examples of such plates include microplates provided with surface functional groups, such as maleic anhydride plates, e.g., Reacti-Bind (trademark) Maleic Anhydride Activated Polystyrene 96-Well Plates (PIERCE); activated amino group plates, e.g., Immobilizer (trademark)-Amino Modules/Plates (Nunc); and carboxyl group plates, e.g., a ELISA plate MS-8796F (96 wells, type C, flat bottom, Carobo) (Sumitomo Bakelite Co., Ltd). Binding of the SITH-1 protein with the solid carrier may be carried out according to the instruction bound to the carrier. More specifically, coupling technology known to persons skilled in the art of the protein with the solid carrier can be used, but any other method can also be used. For example, the protein and the solid carrier can be coupled through a coupling reaction of surface carboxyl groups of a modified solid carrier with amino groups of the protein in the presence of a cross-linking agent, i.e., 1-ethyl-3-(3-dimethylaminopropyl)carbodiimide (EDC). Alternatively, the protein may be mixed with a solid carrier of which the surface is actively esterified with N-hydroxysuccinimide (NHS) in a buffer solution (pH: 6.5 to 9) containing no primary amine groups to bind the carboxy groups on the solid carrier to the amino groups of the protein. Alternatively, amino groups on the solid carrier may be coupled to amino groups of the protein in the presence of a cross-linking agent BS3 (bis[sulfosuccinimidyl]suberate) or DSS (disuccinimidyl suberate), or coupled to thiol groups of the protein in the presence of a cross-linking agent SPDS (N-succinimidyl 3-[2-pyridyldithio)]propionate) or GMBS (N-(4-maleimido butyryloxy) succinimide.

In another embodiment, the SITH-1 and an immobilization tag may be genetically fused. Examples of the immobilization tags include a tag using avidin-biotin binding described below, HisTag, HaloTag (trade mark), and Flag. In the case of HisTag, the surface of a nickel-ionized carrier may be reacted with SITH-1 fused with a plurality of histidine molecules (generally five to ten molecules) to immobilize the protein by the affinity of HisTag to nickel ions.

Binding of SITH-1 Protein to Carrier by Binding Between Biotin and Biotin-Binding Protein In the present invention, the SITH-1 protein may be favorably bound to the carrier by any method. The most preferred method, however, utilizes binding between biotin and a biotin-binding protein. In the present invention, "binding between biotin and a biotin-binding protein" may be referred to as "avidin-biotin binding" in some cases.

Examples of methods for binding of the SITH-1 protein to the carrier by binding between biotin and a biotin-binding protein include A) binding of a biotinylated SITH-1 protein to a carrier comprising a biotin-binding protein bound thereto, B) binding of a biotin- binding protein to a carrier comprising biotin bound thereto, and then binding of a biotinylated SITH-1 protein to the carrier, since most of the biotin-binding proteins are tetramers, and C) binding of a fusion protein of a biotin-binding protein—SITH-1 to a carrier comprising biotin bound thereto.

Detailed explanation will be provided as follows.

Biotin

"Biotin" is a generic name of D-[(+)-cis-hexahydro-2-oxo-1H-thieno-(3,4)-imidazole-4-valeric acid]. It is one of water-soluble vitamins categorized into a vitamin B group, and is also referred to as vitamin $B_7$, vitamin H, or coenzyme R. Biotin strongly binds to avidin, one of the glycoprotein contained in albumen, so that its absorption in human organism is precluded. Thus, large dose of uncooked albumen may cause biotin deficiency disease in some cases.

The term "biotin" throughout the specification includes iminobiotin (Hofmann et al. (1980) Proc Natl Acad Sci USA 77:4666-4668), desthiobiotin (Hirsch et al. (2002) Anal Biochem 308: 343-357, and biotin analogs such as biocytin and biotin sulfoxide, in addition to the biotin described above.

Systems using biotin-avidin (biotin-binding protein) complexes are widely used in the fields of biochemistry, molecular biology, tissue immunology, DNA analysis, and clinical assay. One of the methods of binding the SITH-1 protein to the carrier in the present invention involves use of avidin-biotin binding.

Biotin-Binding Protein

Examples of the biotin-binding proteins preferably used in the present invention include proteins which forms strong bonds with biotin, such as avidin, streptavidin, neutravidin, AVR protein (Biochem. J., (2002), 363: 609-617), bradavidin (J. Biol. Chem., (2005), 280: 13250-13255), rhizavidin (Biochem. J., (2007), 405:397-405), tamavidin (WO02/072817), and mutants thereof. The dissociation constant (KD) with biotin is preferably $10^{-8}$ M or less, more preferably $10^{-10}$ M or less, more preferably $10^{-12}$ M or less. However, this is not always true for the biotin-binding protein which is added to a test sample, and for the biotin-binding protein which is used for blocking a carrier.

Particularly preferred biotin-binding proteins are tamavidin and mutants thereof, which can be highly expressed in *E. coli*. Tamavidin is a biotin-binding protein discovered in an edible mushroom, *Pleurotus cornucopiae* (WO02/072817, Takakura et al. (2009) FEBS J 276: 1383-1397). An example of the mutants of tamavidin is tamavidin exhibiting high binding capability and low nonspecific binding characteristics (PCT/JP2009/64302).

The term "tamavidin" in the present invention refers to tamavidin 1 (TM1), tamavidin 2 (TM2), or a mutant thereof. Specifically, tamavidin of the present invention may be typically a protein having the amino acid sequence of SEQ ID NO: 5 or SEQ ID NO: 7, or a protein encoded by a nucleic acid consisting of the nucleotide sequence of SEQ ID NO: 4 or SEQ ID NO: 6.

Alternatively, tamavidin of the present invention may be a protein which is a mutant of a protein consisting of the amino acid sequence of SEQ ID NO: 5 or SEQ ID NO: 7 or a protein encoded by a nucleic acid consisting of the nucleotide sequence of SEQ ID NO: 4 or SEQ ID NO: 6 and having biotin binding capability similar to that of tamavidin 1 or 2 or high binding and low nonspecific binding characteristics. Throughout the specification, tamavidin 1, tamavidin 2, and mutants thereof may be referred to as collectively tamavidin.

The mutant of tamavidin 1 or 2 may be a protein having an amino acid sequence comprising one or more deletion, substitution, insertion, and/or addition of one or more amino acids in the amino acid sequence of SEQ ID NO: 5 or 7 and having biotin binding capability similar to that of tamavidin 1 or 2.

The definition of "deletion, substitution, insertion, and/or addition of one or more amino acids" is described in the section "SITH-1 protein".

The mutant of tamavidin 1 or 2 may also be a protein having an amino acid sequence sharing an identity of 60% or more, preferably 65% or more, 70% or more, 75% or more, 80% or more, 85% or more, 90% or more, 95% or more, 96% or more, 97% or more, 98% or more or 99% or more, more preferably 99.3% or more with that of SEQ ID NO: 7 or SEQ ID NO: 5 and having biotin binding capability similar to that of tamavidin 1 or 2 or high binding and low nonspecific binding characteristics.

The definition of "percent identity of the amino acid sequence" is described in the section "SITH-1 protein".

Mutants of tamavidin of the present invention further include the following proteins:

(i) A protein which has an amino acid sequence encoded by a nucleic acid consisting of a nucleotide sequence comprising deletion, substitution, insertion, and/or addition of one or more amino acids in the nucleotide sequence of SEQ ID NO: 4 or SEQ ID NO: 6 and which has biotin binding capability similar to that of tamavidin 1 or 2 or high binding and low nonspecific binding characteristics;

(ii) A protein which has an amino acid sequence encoded by a nucleic acid consisting of a nucleotide sequence sharing an identity of 80% or more with the nucleotide sequence of SEQ ID NO: 4 or SEQ ID NO: 6 and which has biotin binding capability similar to that of tamavidin 1 or 2 or high binding and low nonspecific binding characteristics; and (iii) A protein which is encoded by a nucleic acid hybridizable under stringent hybridization conditions with a nucleic acid consisting of a nucleotide sequence complementary to the nucleotide sequence of SEQ ID NO: 4 or SEQ ID NO: 6 and which has biotin binding capability similar to that of tamavidin 1 or 2 or high binding and low nonspecific binding characteristics.

The definition of the terms "deletion, substitution, insertion, and/or addition of one or more nucleotide", "an identity of at least 80%" of the nucleotide sequence, "stringent hybridization conditions" are described in the section "SITH-1 protein".

In addition, when the SITH-1 protein is bound to a carrier by use of the binding between biotin and biotin-binding protein, it is preferable that the "biotin-binding protein" to be used has the biotin-binding activity. Accordingly, without any limitation, it is preferable that the biotin-binding activity of said variants of tamavidin 1 and tamavidin 2 is not significantly reduced compared to the case when the fusion protein is prepared by using the wild types.

Consequently, without any limitation, it is preferable that the variant of tamavidin 1 do not have any modifications in N14, S18, Y34, S36, S78, W82, W98, W110 and D118 in the amino acid sequence of SEQ ID NO:5. The above signatures, "Y34", examples means the tyrosine residue at $34^{th}$ amino acid residue in the amino acid sequence of SEQ ID NO:5. Alternatively, if these amino acid residues are to be modified, they are desirably modified to amino acids having similar properties or structures, in an exemplary case of asparagine (N14), a variant is desirably formed by modifying it to glutamine (Q) or aspartic acid (D), preferably to aspartic acid; in the case of serine (S18, S36, or S78), a variant is desirably formed by modifying it to threonine (T) or tyrosine (Y), preferably to threonine; in the case of tyrosine (Y34), a variant is desirably formed by modifying it to serine (S), threonine (T) or phenylalanine (F), preferably to phenylalanine; in the case of tryptophan (W82, W98, W110), a variant is desirably formed by modifying it to phenylalanine (F), in the case of aspartic acid (D118), a variant is desirably formed by modifying it to glutamic acid (E) or asparagine (N), preferably to asparagine.

Further, s preferable that the variant of tamavidin 2 do not have any modifications in our tryptophan residues (W69, W80, W96, and W108) in the amino acid sequence of SEQ ID NO:7. Alternatively, if these residues are to be modified, they are preferably modified to an amino acid residue having a similar property or structure which is similar to those of tryptophan, e.g., phenylalanine (F). In addition, the amino acid residues in TM2 that are considered to interact directly with biotin (N14, S18, Y34, S36, S76, T78, and D116) are also desirably unmodified. Alternatively, if these amino acid residues are to be modified, they are desirably modified to amino acids having similar properties or structures so that binding to biotin can be maintained; in an exemplary case of asparagine (N14), a variant is desirably formed by modifying it to glutamine (Q) or aspartic acid (D), preferably to aspartic acid; in the case of aspartic acid (D40), a variant is desirably formed by modifying it to asparagine (N); in the case of serine (S18, S36, or S76), a variant is desirably formed by modifying it to threonine (T) or tyrosine (Y), preferably to threonine; in the case of tyrosine (Y34), a variant is desirably formed by modifying it to serine (S), threonine (T) or phenylalanine (F), preferably to phenylalanine; in the case of threonine (T78), a variant is desirably formed by modifying it to serine (S) or tyrosine (Y), preferably to serine; in the case of aspartic acid (D116), a variant is desirably formed by modifying it to glutamic acid (E) or asparagine (N), preferably to asparagine.

Preferred mutants of tamavidin in the present invention include the following modified biotin-binding proteins (PCT/JP2009/64302).

a modified biotin-binding protein which has the amino acid sequence of SEQ ID NO: 7, or an amino acid sequence comprising one to several amino acid mutations in this sequence or having an identity of at least 80% with this sequence and having biotin binding capability, wherein one or more residues selected from the group consisting of:

1) the arginine residue at the 104th site of SEQ ID NO: 7;
2) the lysine residue at the 141st site of SEQ ID NO: 7;
3) the lysine residue at the 26th site of SEQ ID NO: 7; and
4) the lysine residue at the 73rd site of SEQ ID NO: 7;

are replaced with acidic or neutral amino acid residues.

More preferably, the modified biotin-binding protein is selected from the group consisting of:

a modified biotin-binding protein (R104E-K141E) in which the arginine residue at the 104th site is replaced with a glutamic acid residue, and the lysine residue at the 141st site is replaced with a glutamic acid residue, in SEQ ID NO: 7;

a modified biotin-binding protein (D40N-R104E) in which the aspartic acid residue at the 40th site is replaced with a asparagine residue, and the arginine residue at the 104th site is replaced with a glutamic acid residue, in SEQ ID NO: 7;

a modified biotin-binding protein (D40N-K141E) in which the aspartic acid residue at the 40th site is replaced with a asparagine residue, and the lysine residue at the 141st site is replaced with a glutamic acid residue, in SEQ ID NO: 7; and a modified biotin-binding protein (D40N-R104E-K141E) in which the aspartic acid residue at the 40th site is replaced with a asparagine residue, the arginine residue at the 104th site is replaced with a glutamic acid residue, and the lysine residue at the 141st site is replaced with a glutamic acid residue, in SEQ ID NO: 7.

Carrier Comprising Biotin-Binding Protein Bound Thereto

Examples of methods for binding the SITH-1 protein to a carrier through binding biotin between a biotin-binding protein include A) binding of a biotinylated SITH-1 protein to a carrier comprising a biotin-binding protein bound thereto, B) binding of a biotin-binding protein to a carrier comprising biotin bound thereto and then binding of a biotinylated SITH-1 protein to the carrier, since most of the biotin-binding proteins are tetramers and C) binding of a fusion protein of a biotin-binding protein—SITH-1 to a carrier comprising biotin bound thereto.

The carrier comprising a biotin-binding protein bound thereto may be fabricated by direct binding of the biotin-binding protein to the carrier (Embodiment A). Alternatively, a carrier to which a biotin-binding protein is preliminary fixed may be commercially available (Embodiment A). Alternatively, a biotin-binding protein may be bound to a biotinylated carrier through binding between biotin and a biotin-binding protein (Embodiment B). Alternatively, a fusion protein of a biotin-binding protein—SITH-1 may be bound to a carrier comprising biotin bound thereto through binding between biotin and a biotin-binding protein (Embodiment C).

Direct binding of the biotin-binding protein can be carried out, for example, using hydrophobic bond or covalent bond, as described in detail in the method for binding the SITH-1 protein to the carrier. Alternatively, the biotin-binding protein may be directly bound and fixed to a microplate such as NEW ELISA Plate kit (Sumitomo Bakelite Co., Ltd.) according to the instruction attached to the kit. Avidin and streptavidin are commercially available from SIGMA and other companies.

Examples of commercially available carriers comprising biotin-binding proteins bound thereto include, but not limited to, microplates such as Reacti-Bind™ Streptavidin Coated Plates (PIERCE) and Nunc Streptavidin Coated 96 Micro Well™ Plates (Nalge Nunc); and magnetic beads such as Dynabeads M-280 Streptavidin (Dynal) and MagnaBind™ Streptavidin Beads (PIERCE).

Alternatively, the biotin-binding protein may be bound to a carrier which is preliminarily biotinylated, through binding between biotin and a biotin-binding protein.

An exemplary method of biotinylation of the carrier involves use of a biotinylation reagent. Examples of the commercially available biotinylation reagent include, but not limited to, EZ-Link (registered trademark) Sulfo-NHS-Biotin (the length of the linker 13.5 angstroms, the reactive group: primary amine, hereinafter the same order), EZ-Link (registered trademark) Sulfo-NHS-LC-Biotin (22.4 angstroms, primary amine), EZ-Link (registered trademark) Sulfo-NHS-LCLC-Biotin (30.5 angstroms, primary amine), EZ-Link (registered trademark) PFP-Biotin (9.6 angstroms, amine), EZ-Link (registered trademark) Maleimide-$PEO_2$-Biotin (29.1 angstroms, thiol group), EZ-Link (registered trademark) Biotin-$PEO_2$ Amine (20.4 angstroms, carboxyl group), EZ-Link (registered trademark) Biotin-$PEO_3$-LC Amine (22.9 angstroms, carboxyl group), EZ-Link (registered trademark) Biotin-Hydrazide (15.7 angstroms, aldehyde group), EZ-Link (registered trademark) Biotin-LC-Hydrazide (24.7 angstroms, aldehyde group), and EZ-Link (registered trademark) NHS-Iminobiotin (13.5 angstroms, primary amine), which are commercially available from PIERCE.

Using one of these biotinylation reagent, biotin can be bound to a desired carrier such a microplate, microbeads, or a sensor chip by any known process. For example, various carriers having functional groups, such as amino, carboxyl, thiol, tosyl, epoxy, and maleimide groups, and activated ester (for example, magnetic beads, Sepharose beads, agarose beads, latex beads, and microtiter plates) can be used. For example, in the case of the use of a biotinylation reagent containing NHS ester, the reagent may be dissolved in an organic solvent such as dimethyl sulfoxide (DMSO) or phosphate buffer of pH 7 to 9, and then may be added to an immobilization carrier having amino groups to bind biotin thereto. In the case of the use of a biotinylation reagent containing amino groups, the carboxyl groups on the fixing carrier may be converted to activation ester using carbodiimide such as 1-ethyl-3-(3-dimethylaminopropyl) carbodiimide hydrochloride (EDC), followed by addition of a biotinylation reagent solved in buffer solution (pH: about 5) to bind biotin to the carrier. The biotinylated immobilization carrier is preferably blocked with BSA after inactivation of unreacted functional groups.

Commercially available biotinylated carriers can also be used. Typical examples of the biotinylated microplates used include, but not limited to, Reacti-Bind™ Biotin Coated Polystyrene Plates (PIERCE). Examples of the biotinylated microbeads include, but not limited to, magnetic beads, such as BioMag Biotin (available from Polysciences), magnetic nanobeads, such as nanomag (registered trademark)-D biotin and nanomag (registered trademark)-silica biotin available from Corefront, polystyrene microbeads, such as Beadlyte (registered trademark) Biotin Beads (available from Upstate), agarose, such as Biotin Agarose and 2-iminobiotin-Agarose available from Sigma, and highly cross-linked agarose, such as Biotin-Sepharose (available from Biosearch Technologies, Inc.).

The length of the linker binding the carrier to biotin is preferably at least 5 angstroms, more preferably at least 13.5 angstroms.

Biotinylated SITH-1 Protein

In the present invention, biotin may be bound to the SITH-1 protein to prepare a biotinylated SITH-1 protein which is bound to a carrier comprising a biotin-binding protein bound thereto through binding between biotin and a biotin-binding protein.

The carrier comprising a biotin-binding protein bound thereto may be prepared by direct binding of the biotin-binding protein to a carrier as described above, or a carrier to which a biotin-binding protein is preliminary fixed may be commercially available (Embodiment A). Alternatively, a biotin-binding protein may be bound to a biotinylated carrier through binding between biotin and a biotin-binding protein (Embodiment B).

Fabrication of the biotinylated SITH-1 protein is not limited in the present invention. For example, biotin may be bound to the SITH-1 protein using a biotin-labeled kit (for example, EZ-Link (registered trademark) NHS-Lc-Biotin (PIERCE) or Biotin Labeling Kit-NH2 (DOJINDO MOLECULAR TECHNOLOGIES INC.)). Alternatively, a biotinylated SITH-1 may be fabricated as follows: The SITH-1 gene is fused with DNA which encodes peptide comprising a biotinylated sequence to form a vector expressing the fused gene and the gene is expressed as a fused protein with a biotinylated sequence in any host (Schwarz et al., (1988). J. Biol. Chem. 263: 9640-9645).

Nonlimiting examples of such vectors include vectors comprising BioEase (trademark) tags available from Invitrogen. Among them, a pcDNA (trademark) 6 vector is used for mammalian cell expression, a pET 104 vector for *E. coli* expression, and a pMT/BioEase vector for *Drosophila* expression.

Preferably, the method used in the biotinylation of the carrier described above also can be used for biotinylation of the SITH-1 protein. Thus, any biotinylation reagent can be used. Examples of the commercially available biotinylation reagent include, but not limited to, EZ-Link (registered trademark) Sulfo-NHS-Biotin (the length of the linker: 13.5 angstroms, the reactive group: primary amine, hereinafter the same order), EZ-Link (registered trademark) Sulfo-NHS-LC-Biotin (22.4 angstroms, primary amine), EZ-Link (registered trademark) Sulfo-NHS-LCLC-Biotin (30.5 angstroms, primary amine), EZ-Link (registered trademark) PFP-Biotin (9.6 angstroms, amine), EZ-Link (registered trademark) Maleimide-$PEO_2$-Biotin (29.1 angstroms, thiol group), EZ-Link (registered trademark) Biotin-$PEO_2$ Amine (20.4 angstroms, carboxyl group), EZ-Link (registered trademark) Biotin-$PEO_3$-LC Amine (22.9 angstroms, carboxyl group), EZ-Link (registered trademark) Biotin-Hydrazide (15.7 angstroms, aldehyde group), EZ-Link (registered trademark) Biotin-LC-Hydrazide (24.7 angstroms, aldehyde group), and EZ-Link (registered trademark) NHS-Iminobiotin (13.5 angstroms, primary amine), which are commercially available from PIERCE.

Using such a biotinylation reagent, biotin can be bound to the SITH-1 protein through any known process. For example, in the case of the use of a biotinylation reagent containing NHS ester, biotin is dissolved in an organic solvent such as dimethyl sulfoxide (DMSO) or phosphate buffer (pH: 7 to 9) and then may be added to the SITH-1 protein to be bound to biotin. Alternatively, in the case of the use of a biotinylation reagent containing amino groups, the carboxyl group of the SITH-1 protein is converted into activated ester with carbodiimide such as EDC (1-ethyl-3-(3-dimethylaminopropyl) carbodiimide hydroxychloride), followed by addition of a biotinylation reagent in buffer solution (pH: about 5) to bind biotin to the SITH-1 protein.

Before preparation of the biotinylated SITH-1 protein using such a biotinylation reagent, the SITH-1 protein is preferably purified in advance, as described above.

Binding of Biotinylated SITH-1 Protein to Carrier

In the present invention, a carrier comprising a biotin-binding protein bound thereto and a biotinylated SITH-1 protein are prepared and are contacted with each other in order to bind the SITH-1 protein to the carrier by binding between biotin and a biotin-binding protein.

The binding of the biotinylated SITH-1 protein to a carrier can be carried out, but not limited to, through the following procedure. A crude cell homogenate extract containing a biotinylated SITH-1 protein is prepared in a total protein content in the range of 0.1 mg/ml to 5 mg/ml, preferably 0.2 mg/ml to 2 mg/ml. This extract is put into contact with a carrier comprising a biotin-binding protein bound thereto at 4° C. to 40° C., preferably 15° C. to 30° C., for 5 minutes to 2 hours, preferably 30 minutes to 1 hour. During this procedure, the biotinylated SITH-1 protein is immobilized on the carrier comprising the biotin-binding protein bound thereto. Then, the excess crude cell homogenate extract is preferably cleaned off in a buffer solution such as PBS or TBS containing 0.05% to 1%, preferably 0.1% to 0.3% surfactant such as Tween 20.

The binding process by contact of the biotinylated SITH-1 protein with the crude cell homogenate extract virtually involves simultaneous purification and immobilization. Thus, this process does not require any further purification procedure.

Alternatively, a purified biotinylated SITH-1 protein having a concentration of in the range of 0.1 μg/ml to 5 μg/ml may be put into contact with a carrier comprising a biotin-binding protein bound thereto.

4. Contact of Biological Sample with SITH-1 Protein-Bound Carrier

The method of the present invention enables detection of an SITH-1 protein antibody through step 2) of providing a SITH-1 protein-bound carrier, and then step 3) of contacting a biological sample with the SITH-1 protein-bound carrier provided in step 2).

Any approach to contact of the biological sample with the carrier can be employed without limitation. Generally known approaches using a carrier in order to reduce nonspecific binding which causes background signals are, for example, addition of an extract of a bacterium component to a reagent for detection (Japanese Unexamined Patent Application Publication No. 59-99257); addition of a culture component of host cells to a sample, where a vector of the same species as that used in production of a recombinant protein capable of specifically binding to a substance to be detected and containing no gene encoding the protein (Japanese Unexamined Patent Application Publication No. 8-43392); heat treatment of an aqueous extract from cells of the same species as that producing a recombinant protein capable of specifically binding to a substance to be detected and not containing this protein, and addition of its water-soluble fraction to a sample (Japanese Unexamined Patent Application Publication No. 2004-301646).

Addition of Cell Extract

In conventional procedures, the SITH-1 protein antibody cannot readily be detected in samples from patients having autoimmune diseases or healthy subjects having high background factors such as autoantibodies, due to high non-specific binding.

The inventors have found, through extensive study, that the use of the cell homogenate extract on the contact of the biological sample with a carrier allows the SITH-1 protein antibody to be detected even in samples derived from such subjects.

Accordingly, in a preferred embodiment of the present invention, in step 3), a mixture of (a) a biological sample, and (b) a cell homogenate extract prepared from cells of the same species as that of host cells used to express the SITH-1 protein in step 1)

is added to the SITH-1 protein-bound carrier prepared in step 2).

In particular, more remarkably advantageous effects can be achieved in a system of a SITH-1 protein bound to a carrier through binding between biotin and a biotin-binding protein by the following process.

In step 3), a mixture of:

(a) a biological sample, and (b) a cell homogenate extract prepared from a cell of the same species as the host cell used to express the SITH-1 protein, a biotinylated SITH-1 protein, and/or a biotin-binding protein in step 1) or 2)

are added to the SITH-1 protein-bound carrier prepared in step 2).

Cells from which cell homogenate extracts are derived, such as *E. coli* cells, yeast cells, mammalian cells, insect cells, and plant cells, can be used without limitation. Preferred cells are the same species as that of host cells used to express a SITH-1 protein, a biotinylated SITH-1 protein, and/or a biotin-binding protein. For example, in the case of preparation of a SITH-1 protein, a biotinylated SITH-1 protein, and/or a biotin-binding protein using *E. coli*, it is preferred that the cell homogenate extract be also prepared using *E. coli*. In the case of expression of a SITH-1 protein, a biotinylated SITH-1 protein, and/or a biotin-binding protein in a cell-free system, the cell homogenate extract used can be used as it is or as a suspension in a desired buffer solution.

The SITH-1 protein, and/or biotin-binding protein may be extracted and purified from cells originally having these proteins, instead of those being genetically expressed. For example, for the use of tamavidin as a biotin-binding protein, a cell homogenate extract of *Pleurotus* cornucopiae can be used. Accordingly, the cell extract of the present invention includes a cell homogenate extract that originally contains a biotin-binding protein and/or an SITH-1 protein.

The cell used for preparation of the cell homogenate extract may contain any vector, preferably an empty vector. The empty vector is of the same species as that of the vector used in expression of a SITH-1 protein, a biotinylated SITH-1 protein, and/or biotin-binding protein and does not contain a gene which encodes these proteins. The empty vector may further contain any nucleic acid. Alternatively, the empty vector may be different from a vector used in expression of the SITH-1 protein, the biotinylated SITH-1 protein, and/or the biotin-binding protein.

Any cell homogenate extract derived from cells can be used without limitation. For example, protein components, carbohydrate components, and lipid components of cells, and mixture thereof may be used. Preferably, soluble extracts of cells can be used.

The cell homogenate extract can be prepared by a variety of processes without limitation. In general, cells cultured in a proper culture medium are homogenized or solubilized by a physical means such as ultrasonic application, a chemical means using a surfactant, or enzyme treatment, and then a soluble component is isolated by centrifugal separation or filtration. In order to prolong the storage life, preferably the clear liquid prepared by centrifugal separation or filtration is mixed with, for example, a protease inhibitor, or is heated in an autoclave to deactivate various enzymes derived from cells or to suppress their activity. The concentration of the cell homogenate extract can be varied depending on the extent of the occurring nonspecific reaction and may be set in a range sufficient to absorb the nonspecific reaction.

An exemplary method of preparation of the cell homogenate extract, for example, from *E. coli* cells (which may contain a vector which may contain a gene encoding a biotin-binding protein), involves, but not limited to, inoculation of the cells into an LB culture medium containing an antibiotic, shake culture at 25° C. to 37° C. until the absorbance at OD 600 reaches 0.1 to 1, preferably 0.3 to 0.8, addition of 0.01 mM to 5 mM, preferably 0.1 mM to 1 mM IPTG, and then shake culture at 4° C. to 37° C., preferably 15° C. to 37° C., more preferably 25° C. to 37° C. for 2 hr to 48 hr, preferably 4 hr to 24 hr. The bacterial cells are recovered by centrifugal separation from the culture solution, are suspended in a desired buffer solution, and are homogenized. The supernatant liquid after centrifugal separation of the homogenized solution is recovered as a crude *E. coli* extract.

In the case of mixing a crude cell homogenate extract to a biological sample, for example, the sample may be reacted with a crude cell homogenate extract of which the total protein content is controlled to 0.05 mg/ml to 5 mg/ml, preferably 0.5 mg/ml to 5 mg/ml with a desired buffer solution (which may contain BSA, casein, or a commercially available blocking agent) at 4° C. to 37° C., preferably 15° C. to 30° C. for 1 min to 24 hr, preferably 10 min to 4 hr, more preferably 30 min to 2 hr. For a serum biological sample, the serum is generally used after dilution in a cell homogenate extract into 10 to 10000 fold, preferably 100 to 1000 fold, more preferably 100 to 500 fold.

Addition of Biotin-Binding Protein

The inventors have found that the biological sample is preferably put into contact with a carrier in the presence of a biotin-binding protein, in addition to a cell homogenate extract.

Accordingly, in one preferred embodiment of the present invention, in step 3), a mixture of:

(a) a biological sample, and (b-i) a cell homogenate extract prepared from cells of the same species as that of host cells used to express the SITH-1 protein, a biotinylated SITH-1 protein and/or a biotin-binding protein in step 1) or 2), in combination with a biotin-binding protein; or (b-ii) a cell homogenate extract prepared from cells genetically engineered to express a biotin-binding protein, wherein the cells are of the same species as that of host cells used to express the SITH-1 protein, a biotinylated SITH-1 protein and/or a biotin-binding protein in step 1) or 2) is added to the SITH-1 protein-bound carrier prepared in step 2).

In the present invention, addition of a biotin-binding protein to the biological sample can effectively reduce background signal levels.

Such a biotin-binding protein may be any one of the biotin-binding proteins described above, which can be used without limitation. Either the wild type or variants may be used. The biotin-binding activity of the variants may equivalent, higher or lower compared to that of the wild type. In an embodiment, powder of a biotin-binding protein (which may be a naturally occurring protein or may be expressed by genetic engineering) may be added to the sample directly or after its dissolution in a proper solvent. In an alternative embodiment, a mixture of a sample and a cell homogenate extract may be treated with a carrier to which the biotin-binding protein is fixed (for example, the mixture is passed through a column) (step b-i), instead of direct addition of the biotin-binding protein to the sample.

In the case of addition of the biotin-binding protein to a crude cell homogenate extract, the final concentration of the added biotin-binding protein is, but not limited to, 1 μg/ml to 500 μg/ml, preferably 10 μg/ml to 100 μg/ml. The concentration of the biotin-binding protein which is genetically engineered to be expressed in the cells may also substantially be the same as above, but any other concentration is acceptable.

Alternatively, a cell extract containing a biotin-binding protein may be used which is prepared as follows: a gene encoding a biotin-binding protein is expressed by being introduced into host cells and the host cells are homogenized (step b-ii). In this case, the biotin-binding protein can be expressed in a desired host by a well known process to persons skilled in the art. Preferably, the SITH-1 protein, the biotinylated SITH-1 protein, and/or the biotin-binding protein in step 1) or 2) is genetically engineered to be expressed using the same species as that of the host. In the case where the host of the biotin-binding protein differs from the host which expresses the SITH-1 protein or the biotinylated SITH-1 protein by genetic engineering, the cell extract to be mixed and reacted with the biological sample may be derived from both hosts.

In the case of the host being *E. coli*, a gene encoding the biotin-binding protein is incorporated into an expression vector and is introduced into *E. coli*, and *E. coli* is cultivated while expression of protein is induced. Conditions for induction, such as an expression vector and host *E. coli* strains, culture medium component, IPTG concentration, and cultivation temperature can be appropriately determined.

Addition of Biological Sample and Other Components to Carrier

The biological sample, cell homogenate extract, and biotin-binding protein can be added to a carrier by any method. The biological sample, however, must come into contact with the cell homogenate extract and the biotin-binding protein during or before the contact of the biological sample with the carrier. In other words, the biological sample may be put into sufficient contact with the cell homogenate extract during or before the contact with the carrier, and a component derived from the cell homogenate extract, together with the biological sample, is not always added to the carrier finally. For example, a carrier to which the cell homogenate extract component is bound may be prepared, and a biological sample may be added thereto, and then the treated biological sample was used. In an embodiment, before contact of the biological sample with the carrier, the sample is passed through a column to which the cell homogenate extract component has been bound.

After addition of the component, the biological sample and the cell homogenate extract are reacted with the carrier, for example, at 10° C. to 30° C., preferably 20° C. to 30° C., for 10 min to 4 hr, preferably 30 min to 2 hr.

5. Detection of SITH-1 Protein Antibody

In the method of the present invention, the SITH-1 protein antibody is detected in step 3).

Persons skilled in the art can appropriately select the method for detecting the SITH-1 protein antibody. Preferred examples of such methods include immunoassays such as enzyme-linked immuno-sorbent assay (ELISA) and radioimmunoassay (RIA); and other assays such as surface plasmon resonance. After the biological sample is reacted with the immobilized SITH-1 protein by binding between biotin and the biotin-binding protein, the SITH-1 protein antibody is detected.

In the immunoassay, the SITH-1 protein being an antigen is immobilized and is reacted with the SITH-1 protein antibody present in a biological sample, and the reaction product is detected by any method well known to persons skilled in the art. For example, a SITH-1 protein antibody bound to the SITH-1 protein can be detected by using an anti-human antibody, which can recognize and be bound to a human antibody as a secondary antibody. In this procedure, the anti-human antibody is labeled with a fluorescence material, enzyme, or radioisotope, and the fluorescence intensity, enzyme activity, or radiation dose is finally measured to determine the amount of the antibody indirectly.

Any labeling well known to persons skilled in the art may be employed. Alternatively, commercially available fluorescence- or enzyme-labeled anti-human antibodies may be used. Examples of fluorescence labeling include labeling using, for example, fluorescein or rhodamine, and labeling using a fluorescent protein such as a green fluorescent protein (GFP). Enzymes used for enzyme labeling are, but not limited to, peroxidase, alkaline phosphatase, luciferase, and glucose oxidase. Substrates for measurement using these enzymes are commercially available. For example, TBA and substrates for chemiluminescence can be used for peroxidase. Examples of radioisotopes include iodine ($^{125}I$ and $^{121}I$), carbon ($^{14}C$), sulfur ($^{35}S$), and tritium ($^{3}H$), and phosphorus ($^{32}P$) for nucleic acids.

The amount of the antibody present in the biological sample can be readily calculated by comparison with the amount present in a standard preparation, e.g., a standard sample of a healthy subject or a typical patient in the case of clinical samples, using a linear regression computer algorithm. Such assay for detecting an antibody, for example, ELISA is disclosed in Iacobelli et al, Breast Cancer Research and Treatment 11: 19-30 (1988).

In case that the SITH-1 has a low antibody titer or that effect of background signals is significant due to nonspecific binding, the amount of antibody can be more precisely determined by subtracting the observed value of a sample in which the antigen is not immobilized. For example, in case that SITH-1 antibody in a biological sample is low (the antibody titer is low), or in case that non-specific binding of the biological sample (e.g., serum) per se is high, the effect of the background signal due to non-specific binding would be high. Accordingly, the background signal may be appropriately subtracted from the measured value, and the target substance for detection can be determined more precisely. Those skilled in the art can appropriately determine the specific background signal to be subtracted depending on each experimental system.

For example, as described in Examples 2-4, embodiments would be effective wherein the measured value obtained by using a carrier immobilized with the SITH-1 antigen is subtracted by the measured value of the section using the carrier without the immobilized SITH-1 antigen (however, in the section, blocking with BSA or the like has been operated, and the serum containing the anti-SITH-1 antibody (biological sample) has been added).

Alternatively, preferably, the subtraction of the measured value of the section in which any protein to which human has no antibody is immobilized (a non-limiting example is GFP) can lead more precise measurement. The method of immobilization is not limited, and preferably a target protein is biotinylated and is immobilized on a carrier comprising a biotin-binding protein bound thereto, through binding between biotin and a biotin-binding protein.

The detecting method of the present invention enables specific detection of a SITH-1 protein antibody having a low antibody titer in a serum.

II. Carrier Comprising SITH-1 Protein Bound Thereto

The present invention also provides a carrier for detecting the SITH-1 protein antibody in a biological sample.

The carrier of the present invention is a SITH-1 protein-bound carrier. The SITH-1 protein can be bound in various manners, as described above, for example, by utilizing hydrophobic bond, covalent bond, and avidin-biotin binding, and utilizing various tags.

The carrier of the present invention is characterized by being bound to the SITH-1 protein through binding between biotin and a biotin-binding protein. The carrier of the present invention is preferably prepared by:

1) providing a carrier comprising a biotin-binding protein bound thereto and providing a biotinylated SITH-1 protein; and 2) binding the carrier provided in step 1) to the biotinylated SITH-1 protein through binding between biotin and a biotin-binding protein. The biotin-binding protein in 1) may be bound to the carrier directly or through biotin.

III. Kit

The present invention also provides a kit for detecting a SITH-1 protein antibody in a biological sample. The kit of the present invention comprises:

A) a carrier comprising the SITH-1 protein bound thereto; and

B) an agent for diluting the biological sample, which comprises a cell homogenate extract prepared from cells of the same species as that of host cells used to express the SITH-1 protein in A).

The term "a carrier comprising the SITH-1 protein bound thereto" is as defined above.

The agent for diluting the biological sample may be a cell homogenate extract (and a biotin-binding protein) itself, or a diluent for further diluting the cell homogenate extract and the biological sample, for example, a proper buffer solution, a commercially available cell diluent, or a serum diluent.

In the kit of the present invention, preferably the carrier in A) is a carrier comprising the SITH-1 protein bound thereto through binding between biotin and a biotin-binding protein, and the agent in B) comprises:

i) a cell homogenate extract prepared from cells of the same species as that of host cells used to express the SITH-1 protein, a biotinylated SITH-1 protein and/or a biotin-binding protein in A), in combination with a biotin-binding protein; or ii) a cell homogenate extract prepared from cells genetically engineered to express a biotin-binding protein, wherein the cells are of the same species as that of host cells used to express the SITH-1 protein, the biotinylated SITH-1 protein and/or the biotin-binding protein in A).

The term "a carrier comprising a SITH-1 protein bound thereto through binding between biotin and a biotin-binding protein" is as defined above.

The terms "a cell homogenate extract prepared from a cell of the same species as the host cell used to express the SITH-1 protein, a biotinylated SITH-1 protein, and/or a biotin-binding protein in A)", "a biotin-binding protein", "a cell homogenate extract prepared from cells genetically engineered to express a biotin-binding protein, wherein the cells are of the same species as that of host cells used to express the SITH-1 protein, a biotinylated SITH-1 protein, and/or a biotin-binding protein" are also as defined above.

Alternatively, the kit of the present invention comprises:

A) the SITH-1 protein;

B) a carrier for immobilizing the SITH-1 protein in A); and

C) an agent for diluting a biological sample, which comprises a cell homogenate extract prepared from cells of the same species as that of host cells used to express the SITH-1 protein in A).

"The SITH-1 protein" is preferably purified before binding to the carrier by means of hydrophobic bond or covalent bond. In the case of using various tags and binding between biotin and a biotin-binding protein, a SITH-1 protein to which the tag or biotin is bound is preferred, as described above.

"The carrier for immobilizing the SITH-1 protein in A)" may be the carrier described above, and is preferably a carrier which is treated for being bound to "the SITH-1 protein".

The terms "cell homogenate extract prepared from cells of the same species as that of host cells used to express the SITH-1 protein in A)" and "agent for diluting a biological sample" are also as defined above.

In a preferred embodiment of the kit of the present invention, the SITH-1 protein in A) is biotinylated,
the carrier in B) is directly or indirectly bound to a biotin-binding protein, and
the agent in C) is an agent for diluting the biological sample, which comprises:

i) a cell homogenate extract prepared from cells of the same species as that of host cells used to express the SITH-1 protein, a biotinylated SITH-1 protein and/or a biotin-binding protein in A) or B), in combination with a biotin-binding protein; or ii) a cell homogenate extract prepared from cells genetically engineered to express a biotin-binding protein, wherein the cells are of the same species as that of host cells used to express the SITH-1 protein, a biotinylated SITH-1 protein and/or a biotin-binding protein in A) or B).

The method of biotinylation of the SITH-1 protein and the carrier directly or indirectly bound to a biotin-binding protein are as defined above.

"A cell homogenate extract prepared from a cell of the same species as that of host cells used to express the SITH-1 protein, a biotinylated SITH-1 protein and/or a biotin-binding protein in A) or B)", "a biotin-binding protein", "a cell homogenate extract prepared from cells genetically engineered to express a biotin-binding protein, wherein the cells are of the same species as that of host cells used to express the SITH-1 protein, a biotinylated SITH-1 protein and/or a biotin-binding protein in A) or B)", and "an agent for diluting a biological sample" are also defined as above.

EXAMPLES

The present invention will now be described in more detail by way of the following examples, which are not intended to limit the technical scope of the invention. Based on the detailed description, modifications and changes will be apparent to those skilled in the art, and such modifications and changes fall within the technical scope of the invention.

In the examples 1-3 described below, a fusion protein between a human herpes virus 6 (HHV-6)-derived SITH-1 protein and a biotinylation sequence (BioEase tag, Invitrogen) was expressed in *E. coli* cells, and an *E. coli* crude extract obtained from these cells was directly reacted with a microplate, on which tamavidin 2 (hereinafter referred to as "TM2") was immobilized, to thereby bind the fusion protein to the microplate through tamavidin-biotin binding.

The SITH-1 protein-bound plate thus obtained was reacted with human serum diluted with an *E. coli* crude extract (supplemented with rabbit anti-SITH-1 antibody; since commercially available human sera are free from anti-SITH-1 antibody, those supplemented with serial dilutions of rabbit anti-SITH-1 antibody (antiserum) were used as analytes in this test) to measure the titer of anti-SITH-1 antibody contained in the human serum.

Example 1

Vector Construction for Expression of Fusion Protein Between SITH-1 and Biotinylation Sequence (BioEase Tag)

A gene was designed to encode a fusion protein having a BioEase tag located at the N-terminal end of the SITH-1 protein. This BioEase tag is a peptide tag containing a sequence to be biotinylated in vivo (i.e., within *E. coli* cells in this case) by the action of an endogenous biotinylation enzyme. The amino acid sequence of the BioEase-SITH-1 fusion protein is shown in SEQ ID NO: 8 and the nucleotide sequence encoding the same is shown in SEQ ID NO: 9.

1-1. Primer Design

To construct a BioEase-SITH-1 fusion gene, primers for amplification of the SITH-1 gene were first designed. Namely, the following two primers were designed: a primer consisting of a DNA sequence encoding an N-terminal region of the SITH-1 protein (SITH1NtermGW-F) and a primer consisting of a DNA sequence encoding a C-terminal region of the SITH-1 protein in the reverse direction (SITH1CtermGW-R).

The primers for construction of a fusion gene between SITH-1 and BioEase tag are summarized in Table 1.

TABLE 1

| SITH-1 gene amplification primers | | |
|---|---|---|
| Name | Sequence | Length |
| SITH1NtermGW-F | GGATATGAAGAAAAAGTGTC (SEQ ID NO: 10) | 20 mer |
| SITH1CtermGW-R | TTACACATTCATTTCAGTTT (SEQ ID NO: 11) | 20 mer |

1-2. PCR

The DNA of an expression vector carrying the SITH-1 gene (ORF) (SEQ ID NO: 2) with the FLAG-tag (PCT/JP2008/67300) was used as a template to amplify a SITH-1 region by PCR with the primers SITH1NtermGW-F and SITH1CtermGW-R. PCR was accomplished by using a GeneAmp PCR System 9600 (PERKIN ELMER) in 20 µl reaction solution containing template DNA (500 ng), 10× ExTaq buffer (2 µl, TaKaRa), 2.5 mM dNTP (1.6 µl), primers (20 pmoles each) and 5 U/µl ExTaq (0.1 µl) under reaction conditions: 96° C. for 3 minutes, (95° C. for 1 minute, 60° C. for 1 minute, 72° C. for 2 minutes)×20 cycles, and 72° C. for 6 minutes. As a result, a PCR product of 477 bp was obtained.

1-3. Cloning

The SITH-1 gene obtained by PCR was cloned into vector pCR8/GW/TOPO (Invitrogen). Ligation reaction was performed according to the manufacturer's instructions bound to the vector kit. The DNA was introduced into *E. coli* TB1 by electroporation and the plasmid DNA was extracted in a routine manner (Sambrook et al. 1989, Molecular Cloning, A laboratory manual, 2nd edition). Each plasmid for which the presence of an insert was confirmed was analyzed with M13 primers (TaKaRa) and an ABI PRISM fluorescent sequencer (Model 310 Genetic Analyzer, Perkin Elmer) to determine its nucleotide sequence, which was then confirmed to have no mutation in comparison with the sequence of the designed gene.

The plasmid carrying the SITH-1 gene was used as an entry clone and subjected to recombination reaction with pET104.1 destination vector (Invitrogen), which is an expression vector for a BioEase tag-fused protein, using a Gateway System. The recombinant product was transformed into *E. coli* TB1 and the plasmid DNA was extracted. This plasmid was further transformed into *E. coli* BL21(DE3). The resulting *E. coli* colonies were each used as a template to amplify an insert gene region by PCR with SITH1NtermGW-F and SITH1CtermGW-R to thereby confirm the presence or absence of the insert gene.

In the manner described above, a vector for BioEase tag-fused SITH-1 protein expression, BioEase-SITH1/pET104.1 was completed.

1-4. *E. coli* Expression

*E. coli* BL21(DE3) carrying BioEase-SITH1/pET104.1 or *E. coli* BL21 carrying pTrc99A alone (as a control) was inoculated into LB medium (50 ml) containing the antibiotic ampicillin (final concentration: 100 μg/ml) and cultured with shaking at 30° C. until the absorbance at OD600 reached 0.5. Then, 1 mM IPTG was added and the *E. coli* cells were cultured with shaking at 30° C. for an additional 5 hours. The cultured solution (50 ml) was centrifuged to collect the cells. The cells were suspended in 3 ml of 0.1M HEPES/KOH (pH 7.4) and then homogenized by ultrasonication. The homogenate was centrifuged (15,000 rpm), and the resulting supernatant was used as an *E. coli* crude extract.

To confirm the expression of the BioEase tag-fused SITH-1 protein, proteins contained in each crude extract were fractionated by SDS-PAGE and analyzed by Western blotting. In Western blotting for detection of BioEase tag-fused SITH-1, rabbit anti-SITH-1 antibody (unpublished) and alkaline phosphatase-labeled anti-rabbit IgG antibody (BIO RAD) were used.

The results obtained are shown in FIG. 1A. A band of approximately 30 kDa, which was not found in the control, was detected from the BioEase tag-fused SITH-1-expressing *E. coli* cells. This size was substantially equal to the molecular weight (28.6 kDa) of BioEase tag-fused SITH-1.

Further, horseradish peroxidase-labeled streptavidin was used in place of anti-SITH-1 antibody to detect signals. The results obtained are shown in FIG. 1B. In the control, almost no signal was detected, whereas two thick bands originating from proteins that react with streptavidin (i.e., appear to be biotinylated) were detected from the BioEase tag-fused SITH-1-expressing *E. coli* crude extract. Among them, the upper band was further found to have substantially the same size as the band detected above by Western blotting. These results indicated that the expression of biotinylated SITH-1 was successful.

In addition to the above extracts, for use in the subsequent ELISA experiment, additional *E. coli* crude extracts were prepared in the same manner from *E. coli* BL21 carrying pTrc99A or TM2/pTrc99A (WO 02/072817) after being cultured in the presence of IPTG.

Example 2

ELISA Detection of Anti-SITH-1 Antibody in Human Serum

Purified TM2 was immobilized on a microplate using a New ELISA plate kit (Sumitomo Bakelite Co., Ltd., Japan) Immobilization was accomplished according to the manufacturer's instructions attached to the kit.

The BioEase tag-fused SITH-1 protein-expressing *E. coli* crude extract obtained in Example 1 was adjusted to have a total protein concentration of 2 mg/ml with 0.1M HEPES/KOH (pH 7.4), 100 μl of which was then added to the TM2-immobilized plate (Sumitomo Bakelite Co., Ltd., Japan, New ELISA). The plate was allowed to stand at room temperature for 1 hour to thereby bind the BioEase tag-fused SITH-1 protein onto the TM2-immobilized plate through tamavidin-biotin binding. Then, each well in the plate was washed three times with 0.1% Tween 20-containing TBS buffer (TBST), followed by addition of a 5 μg/ml BSA/TBST solution in a volume of 250 μl per well. The plate was allowed to stand at room temperature for 1 hour to block each well. Then, each well was washed three times with TBST.

Next, human serum (Human Serum pool, Cosmo-Bio, Inc.) was diluted 100-fold with PBS or with the 1 mg total soluble protein/ml pTrc99A-carrying *E. coli* crude extract or the 1 mg total soluble protein/ml TM2/pTrc99A-carrying *E. coli* crude extract prepared in (1-4) of Example 1. To the resulting solution, rabbit anti-SITH-1 antibody was added in serial dilution to give a volume ratio of 1/500, 1/1000, 1/2000, 1/4000 or 1/8000. These human serum dilutions (containing anti-SITH-1 antibody) were added in 100 μl volumes to the plate on which the BioEase tag-fused SITH-1 protein was immobilized through biotin-tamavidin 2 binding, followed by incubation for 1 hour at room temperature.

It is expected that the antibody titer in serum of the rabbit anti-SITH-1 antibody (anti-serum) is about 50 times higher compared to the SITH-1 antibody titer in serum of a patient with a typical depression (mood disorder). Accordingly, pseudo sample for serum of a patient with a typical depression can be prepared by mixing 1/50 volume of rabbit anti-SITh-1 antibody (anti-serum) to a commercially available human serum (of a healthy person). Accordingly, the dilution rates of the antibody as discussed above provide samples similar to those when serum of depression patients are used after about 10 to 80 folds dilutions.

Further, to confirm the effect of TM2 in the *E. coli* crude extracts used for serum dilution, a solution was prepared to contain purified TM2 at a final concentration of 50 μg/ml in PBS or in the above pTrc99A-carrying *E. coli* crude extract. Human serum was diluted 100-fold with this solution, and to the resulting solution, rabbit anti-SITH-1 antibody was added in serial dilution to give a volume ratio of 1/500, 1/1000, 1/2000, 1/4000 or 1/8000, as in the case mentioned above. These dilutions were added in 100 μl volumes to the plate on which BioEase tag-fused SITH-1 was immobilized, followed by incubation for 1 hour at room temperature. On the other hand, as a control, a TM2-immobilized plate onto which nothing was bound was also blocked as described above. Human serum was diluted 100-fold with the same PBS solution or the same pTrc99A-carrying or TM2/pTrc99A-carrying *E. coli* crude extract (1 mg total soluble protein/ml) as used above, or alternatively, with the purified TM2-supplemented PBS or with the purified TM2-supplemented pTrc99A-carrying *E. coli* crude extract, followed by addition of serially diluted rabbit anti-SITH-1 antibody. The resulting dilutions were added in 100 μl volumes to the control plate and incubated at room temperature for 1 hour.

The thus prepared human serum samples, which were diluted with various diluents and supplemented with serially diluted rabbit anti-SITH-1 antibody, were each reacted with the BioEase tag-fused SITH-1 protein immobilized on the carrier, followed by washing three times with TBST. Then, to detect each of the rabbit anti-SITH-1 antibody bound to SITH-1 and the human IgG in serum which is presumed to be bound non-specifically in each well, a mixture of horseradish peroxidase-labeled goat anti-rabbit IgG antibody and peroxidase-labeled goat anti-human IgG antibody, each of which was diluted 5000-fold with TBST, was added in a volume of 100 µl per well, followed by incubation for 1 hour at room temperature. Then, each well was washed three times with TBST and peroxidase activity was detected. The activity was measured as follows: To each well, SuperSignal ELISA Pico Chemiluminescent Substrate (PIERCE) was added in a volume of 100 µl and allowed to stand for 5 minutes at room temperature, followed by measuring the luminescence intensity with a plate reader Infinite M200 (TECAN). It should be noted that the data also include a luminescence intensity value measured at each concentration of rabbit anti-SITH-1 antibody for the control section sample (i.e., the region wherein the TM2 plate on which BioEase tag-fused SITH-1 was not immobilized, but which was blocked and treated with human serum containing anti-SITH-1 antibody at each concentration). The value of the control section was subtracted from the luminescence intensity value of each BioEase tag-fused SITH-1-immobilized section. The resulting value was defined as the detected amount of anti-SITH-1 antibody contained in the serum. Further, the S/N ratio was calculated by the equation shown below to compare the effect of each serum dilution.

S/N ratio=Detected amount of anti-SITH-1 antibody in a sample containing anti-SITH-1 antibody at each concentration/Detected amount of anti-SITH-1 antibody in a sample free from anti-SITH-1 antibody The equation shows that the detection sensitivity is higher when S/N ratio is larger.

The results obtained are shown in FIGS. 2 and 3. The anti-SITH-1 antibody contained in the serum showed non-specific binding in most of the serum sections diluted with PBS, and a high level of luminescence intensity was also detected in the sections free from anti-SITH-1 antibody. Moreover, this non-specific binding was not improved in the presence of 50 µg/ml TM2. In contrast, in the serum sections diluted with the pTrc99A-carrying *E. coli* crude extract or with the TM2/pTrc99A-carrying *E. coli* crude extract, or in the serum sections diluted with the pTrc99A-carrying *E. coli* crude extract supplemented with 50 µg/ml TM2, luminescence intensity was significantly low in sections without addition of the SITH-1 antibody, and non-specific binding was dramatically reduced (FIG. 2).

As shown in FIG. 3, the S/N ratio was particularly high in the samples diluted with the pTrc99A-carrying *E. coli* crude extract supplemented with 50 µg/ml TM2 and in the samples diluted with the TM2/pTrc99A-carrying *E. coli* crude extract.

These results indicated that in the measurement system using a TM2 plate on which BioEase tag-fused SITH-1 was immobilized, dilution of human serum with a TM2-containing *E. coli* crude extract allowed a reduction of non-specific binding originating from the human serum, thereby enabling the sensitive and quantitative detection of anti-SITH-1 antibody even at a very low concentration.

Example 3

ELISA Analysis with Patient-Derived Serum Analytes 3-1. Measurement of Anti-SITH-1 Antibody Titers in Human Serum Using TM2 Plate and Biotinylated SITH-1

Six patient sera found to have SITH-1 antibody (obtained from two patients with chronic fatigue syndrome, three patients with depression and one patient with Crohn's disease) and six sera from normal subjects who were difficult to diagnose by the fluorescent antibody method due to high background arising from autoantibodies were used and measured for their serum antibody titers. It should be noted that the patient sera and the control sera from normal subjects were collected and tested under approval by the ethical committee of Jikei University School of Medicine (Japan), Osaka University Graduate School of Medicine (Japan) or Osaka City University Graduate School of Medicine (Japan).

For measurement of anti-SITH-1 antibody titers in patients, the samples diluted 40- to 160-fold were used in the fluorescent antibody method. The control sera from normal subjects used in this study were six analytes which had 40- to 80-fold anti-nuclear antibody or anti-cytoplasm antibody and whose SITH-1 antibody titers were difficult to measure by the fluorescent antibody method.

The fluorescent antibody method was performed as follows. The antigen used in the fluorescent antibody method was prepared as follows: 293T cells cultured on 8-chamber slides (Lab-Tek) were transfected with an expression vector for SITH-1 (pEGFP-N1 vector (Clontech) whose EGFP region had been replaced by the open reading frame of SITH-1) and, after 24 hours, were then fixed with cold acetone for 5 minutes. On the other hand, each human serum was serially diluted in two-fold increments (i.e., 20-fold, 40-fold, 80-fold or 160-fold) with PBS(−: free from calcium and magnesium) containing 0.2% BSA and 0.2% Tween 20 and used as a primary antibody. The primary antibody and the antigen were reacted at 37° C. for 1 hour and then washed three times with PBS(−) containing 0.2% Tween 20 for 30 minutes. As a secondary antibody, Alexa Fluor® 488 anti-human IgG (Invitrogen) was diluted 500-fold and reacted at 37° C. for 1 hour. After washing with PBS(−) containing 0.2% Tween 20 for 30 minutes, each sample was observed under a fluorescent microscope. The maximum dilution factor of the primary antibody which gave a stained image unique to SITH-1 was defined as an antibody titer, as measured by the fluorescent antibody method.

ELISA analysis using a TM2 NEW plate was performed according to the procedures described in Example 2. A BioEase tag-fused SITH-1-expressing *E. coli* crude extract was diluted to 2 mg total protein/ml with 0.1M HEPES/KOH (pH 7.4) and added to a TM2 New ELISA plate in a volume of 100 µl per well. The plate was allowed to stand at room temperature for 1 hour to thereby bind the BioEase tag-fused SITH-1 protein onto the plate through tamavidin-biotin binding. Then, each well in the plate was washed three times with 0.1% Tween 20-containing TBS buffer (TBST). In this way, a recombinant SITH-1 protein-immobilized plate was prepared.

Next, the above patient-derived human sera were diluted 100-fold with any one of the following solutions 1) to 3):

1) a solution containing 1% casein in TBS-T (Tris-buffered saline, containing 0.1% Tween 20);

2) an *E. coli* crude extract, i.e., the supernatant of an *E. coli* (BL21) lysate (without IPTG induction), which was treated with BugBuster Protein Extraction Reagent (Novagen) in a volume of 5 ml per gram of *E. coli* pellet and centrifuged at 3,000 g for 10 minutes; or 3) a 5 mg total protein/ml TM2-expressing *E. coli* crude extract (with IPTG induction), which was prepared as described in Example 1.

These serum samples were added in 100 µl volumes to the BioEase tag-fused SITH-1 protein-bound plate, followed by incubation for 1 hour at room temperature and further washing three times with TBST.

As a control, serum-free PBS, a serum-free *E. coli* crude extract, or a serum-free TM2-expressing *E. coli* crude extract was added in 100 μl volumes, followed by incubation for 1 hour at room temperature and further washing three times with TBST.

Then, as a secondary antibody, anti-human IgG-HRP antibody (Jackson Immuno Research) was diluted 5000-fold with TBST and added in 100 μl volumes, followed by incubation for 1 hour at room temperature. Then, the plate was washed three times with TBST and color-developed with TMB1 Component HRP Microwell Substrate (BioFX laboratories) to detect peroxidase activity. It should be noted that the absorbance of wells containing the developer TMB1 alone was subtracted from the absorbance of each test sample.

The absorbance values observed are shown in FIGS. 4 to 6. As shown in FIG. 4, in the case of the serum samples diluted (pre-treated) with casein-containing TBS-T before being provided for ELISA, the absorbance was 3.56±0.12 in patients and 3.65±0.19 in normal subjects, thus indicating that there was no great difference between patients and normal subjects. In contrast, as shown in FIG. 5, in the case of the serum samples diluted with the *E. coli* crude extract, the absorbance was 1.84±1.14 in patients and 1.26±0.14 in normal subjects, thus indicating that the patients tended to show larger values. Moreover, as shown in FIG. 6, in the case of the serum samples diluted with the TM2-expressing *E. coli* crude extract, the absorbance was 1.05±0.27 in patients and 0.43±0.09 in normal subjects, thus indicating that there was a significant difference (statistical significance at 0.1% significance level) between patients and normal subjects.

In this study, a sufficient difference was observed between patients and normal subjects although serum samples which were difficult to diagnose by the fluorescent antibody method were used. This suggested that ELISA analysis using the TM2 plate and biotinylated SITH-1, particularly in combination with the TM2-expressing *E. coli* crude extract as a serum diluent, was a practical method.

3-2. Measurement of Anti-SITH-1 Antibody Titers in Human Serum Using Nickel Plate and His Tag-Fused SITH-1 Protein In this example, a QIAGEN nickel plate commercially available as an ELISA plate was used in combination with a histidine tag (His tag)-bound SITH-1 protein to perform ELISA for antibody measurement.

The His-tagged SITH-1 protein was expressed as a fusion protein with Trx-Tag (Thioredoxin) composed of 109 amino acids obtained from pET-32a-ru(+) DNA, for the purpose of preventing the SITH-1 protein from forming an insoluble inclusion body within *E. coli* cells.

Into an *E. coli* cold-shock vector pCold I (TaKaRa Bio), Trx (Thioredoxin) composed of 109 amino acids obtained from pET-32a(+) DNA was inserted in-frame with a His tag. Further, SITH-1 or EGFP was inserted in-frame downstream of Trx. In this way, His tag-Trx-SITH-1 or His tag-Trx-EGFP was constructed. The plasmid thus completed was introduced into *E. coli* (BL21) cells. These *E. coli* cells were cultured with shaking in LB liquid medium (supplemented with IPTG at a final concentration of 1.0 mM) at 15° C. for 24 hours to induce protein expression. The *E. coli* pellet was collected by centrifugation and then treated with BugBuster Protein Extraction Reagent (Novagen) in a volume of 5 ml per gram of *E. coli* pellet to extract *E. coli* proteins. This extract was centrifuged at 3,000 g for 10 minutes, and the resulting supernatant was used as a His tag-SITH-1 protein-expressing *E. coli* crude extract.

ELISA analysis using a nickel plate was performed as follows. Ni-NTA HisSorb Strips (QIAGEN) were reacted with the above His tag-SITH-1-expressing *E. coli* crude extract at room temperature for 1 hour. After washing three times with PBS(−) containing 0.5% Tween 20, anti-SITH-1 rabbit serum or the above patient-derived human serum was added and reacted at room temperature for 1 hour. After washing three times with PBS(−) containing 0.5% Tween 20, anti-rabbit IgG-HRP antibody (Roche, diluted 5,000-fold) or anti-human IgG-HRP antibody (Jackson Immuno Research, diluted 5,000-fold) was used as a secondary antibody. Color development was performed using TMB1 Component HRP Microwell Substrate (BioFX laboratories).

First, to confirm the usefulness of the nickel plate and the His-tagged SITH-1 protein, ELISA for antibody measurement was performed with anti-SITH-1 rabbit serum.

The rabbit serum was diluted 100- or 500-fold for use in ELISA. The results obtained with these dilutions are shown in FIGS. 7 and 8, respectively. The results indicated that in the case of using the rabbit serum, the nickel plate and the His-tagged SITH-1 protein could be used for antibody measurement.

Next, the same human sera as used in 3-1 above (6 patient sera and 6 control sera from normal subjects) were used for antibody measurement using the nickel plate and the His-tagged SITH-1 protein. As a protein control to confirm non-specific binding, a His-tagged EGFP protein was used.

Each serum was studied in both 100-fold and 500-fold dilution. The diluents used were 1% bovine serum albumin (BSA) and the same *E. coli* crude extract as used in (3-1) above. It should be noted that the buffer used for serum reaction was PBS(−) and blocking was performed with 0.2% BSA-containing PBS. Likewise, washing was performed with 0.05% Tween 20-containing PBS(−).

The results obtained are shown in FIGS. 9 and 10. In the serum samples diluted 100-fold, 1% BSA and the *E. coli* crude extract each showed no great difference in antibody titers between patients and normal subjects. In contrast, in the serum samples diluted 500-fold, 1% BSA and the *E. coli* crude extract each tended to show higher antibody titers in patients than in normal subjects, although the difference in antibody titers was smaller than that observed with the method described in (3-1).

Example 4

ELISA Detection of Anti-SITH-1 Antibody in Human Serum Using Magnetic Beads

In this example, various serum diluents were studied for their effect on the detection of SITH-1 antibody at very low concentrations in the system using biotinylated magnetic beads on which TM2-fused SITH-1 was immobilized.

4-1. Primer Design

To construct a SITH1-TM2 fusion gene, primers for fusing the SITH-1 and TM2 genes via a linker (5×linker: GGGGSGGGGSGGGGSGGGGSGGGGS) (SEQ ID NO: 12) were first designed.

Namely, the following two primers were designed: a primer consisting of a DNA sequence encoding a C-terminal region of SITH-1 on the 5' side, the linker in the middle, and an N-terminal region of TM2 on the 3' side (SITH1C-5xlink-TM2N-F) (SEQ ID NO: 13); and a primer consisting of a DNA sequence encoding the N-terminal region of TM2 on the 5' side, the linker in the middle, and the C-terminal region of SITH-1 on the 3' side, each of these elements being encoded in the reverse direction (SITH1C-5xlink-TM2N-R) (SEQ ID NO: 14).

Next, the following two primers were designed: a primer consisting of a 5' region including an N-terminal region of SITH-1 and an EcoRI restriction enzyme cleavage site (CCATGG) located upstream thereof (SITH1 5' EcoRI-F) (SEQ ID NO: 15); and a primer consisting of a sequence encoding a 3' region of the TM2 gene and a BamHI restriction enzyme cleavage site (GGATCC) located downstream thereof (TM2CtermBam) (SEQ ID NO: 16). The primers for construction of a fusion gene between SITH-1 and TM2 are summarized in Table 2.

TABLE 2

Primers for construction of a fusion gene between SITH-1 and TM2

| Name | SEQ ID NO | Sequence | Length |
|------|-----------|----------|--------|
| SITH1C-5' EcoRI-F | 15 | AAAGAATTCGGATATGAAGAAAAAGTGTC | 29 mer |
| SITH1C-5xlink-TM2N-F13 | | CCGAAAACTGAAATGAATGTGggtggcggtggc agcggtggcggtggcagcggtggcggtggcagcggtggcg gtggcagcggtggcggtggcagcTCAGACGTTCAATCTTCACTC | 117 mer |
| SITH1C-5xlink-TM2N-R14 | | GAGTGAAGATTGAACGTCTGAgctgccaccgcca ccgctgccaccgccaccgctgccaccgccaccgctgccacc gccaccgctgccaccgccaccCACATTCATTTCAGTTTTCGG | 117 mer |
| TM2CtermBam | 16 | TTTGGATCCTTACTTCAACCTCGGTGCG | 28 mer |

The restriction enzyme recognition sites are underlined. The linker sequences are indicated in small letters.

4-2. PCR

To construct a SITH1-TM2 fusion gene, PCR was performed in two steps.

In the first step of PCR, a plasmid obtained by integrating the SITH-1 gene (ORF) (SEQ ID NO: 2) into FLAG Expression Vector (SIGMA) was used as a template to amplify a SITH-1 region with the primers SITH1 5' EcoRI-F and SITH1C-5xlink-TM2N-R, and a plasmid obtained by integrating the TM2 gene into vector pTrc99A (WO02/072817) was used as a template to amplify a TM2 region with the primers SITH1C-5xlink-TM2N-F and TM2CtermBam.

PCR was accomplished in the same manner as shown in Example 1-2 above. As a result, a PCR product of 579 bp was obtained for the SITH-1 region, while a PCR product of 528 bp was obtained for the TM2 region. These PCR products were each used as a template to perform the second step of PCR with the primers SITH1 5' EcoRI-F and TM2CtermBam. As a result, a PCR product of 990 bp was obtained.

4-3. Cloning

The SITH1-TM2 fusion gene obtained by PCR was cloned into vector pCR4Blunt TOPO (Invitrogen) in the same manner as shown in Example 1-3 above. The plasmid carrying the fusion gene was further double-digested with EcoRI and BamHI to collect a DNA fragment containing the fusion gene. This fragment was cloned into E. coli expression vector pTrc99A (Pharmacia) which had been digested with EcoRI and BamHI. In the manner described above, a vector for SITH-1-TM2 fusion protein expression, SITH1-TM2/pTrc99A, was completed. The nucleotide sequence encoding SITH1-TM2 in the expression vector SITH1-TM2/pTrc99A is shown in SEQ ID NO: 17, and the amino acid sequence encoded thereby is shown in SEQ ID NO: 18.

In the 5' side of SITH1-TM2, two amino acid residues are added downstream of the translation initiation methionine (nucleotides 4-9 in SEQ ID NO: 17, amino acid residues 2-3 in SEQ ID NO: 18) because the EcoRI site was used for integration into pTrc99A. These amino acid residues are followed by the SITH-1 sequence (nucleotides 10-483 in SEQ ID NO: 17, amino acid residues 4-161 in SEQ ID NO: 18), 5xlinker (nucleotides 484-558 in SEQ ID NO: 17, amino acid residues 162-186 in SEQ ID NO: 18), and the TM2 sequence (excluding Met) (nucleotides 559-981 in SEQ ID NO: 17, amino acid residues 187-326 in SEQ ID NO: 18).

4-4. E. coli Expression

E. coli BL21 carrying SITH1-TM2/pTrc99A was cultured in the same manner as shown in Example 1-4 above. The cultured solution (50 ml) was centrifuged to collect the cells. The cells were suspended in 3 ml of 0.1 M HEPES/KOH (pH 7.4) and then homogenized by ultrasonication. The homogenate was centrifuged (15,000 rpm), and the resulting supernatant was used as an E. coli crude extract. Expression of the TM2-fused SITH-1 protein was confirmed by Western blotting.

For detection of SITH-1, rabbit anti-SITH-1 antibody (i.e., anti-SITH-1 antibody (antiserum) prepared from rabbits immunized with a purified product of SITH-1 expressed in E. coli cells) and alkaline phosphatase-labeled anti-rabbit IgG antibody (BIO RAD) were each diluted 1000-fold and used. As a result, a band of approximately 35 kDa was detected from the TM2-fused SITH-1-expressing E. coli cells. This size was substantially equal to the molecular weight (34.8 kDa) of TM2-fused SITH-1. It should be noted that E. coli crude extracts were also prepared in the same manner as shown above from E. coli BL21 carrying pTrc99A or TM2/pTrc99A (Takakura et al. (2009) FEBS J. 276:1383-1397) after being cultured in the presence of IPTG.

4-5. Preparation of TM2-Fused SITH-1-Immobilized Magnetic Beads

To 1 mL (30 mg beads/mL) of magnetic beads (Dynabeads M-270 Amine, DynalBiotech), 1 mL of 10 mM NHS-Lc-Lc-Biotin (PIERCE) was added. By mixing end-over-end at room temperature for 30 minutes, biotin was covalently bonded to the magnetic beads through reaction between amino groups and NHS active ester groups. Then, the magnetic beads was washed twice with a 0.1% BSA/0.01% Tween 20/PBS solution, and finally suspended in PBS buffer. The resulting magnetic beads (30 mg beads/mL PBS) were used as biotinylated magnetic beads.

TM2-fused SITH-1 was expressed in E. coli cells in the same manner as shown in Example 4-4 above, and the E. coli crude extract thus prepared was diluted with 0.1 M HEPES/KOH (pH 7.4) to give a total soluble protein concentration of 5 mg/ml, to which the biotinylated magnetic beads were then added. By mixing end-over-end at room temperature for 1 hour, TM2-fused SITH-1 was immobilized on the magnetic beads through tamavidin-biotin binding. Then, the magnetic beads were washed three times with 0.2% Tween 20-containing TBS buffer (TTBS).

In addition, a crude extract of TM2-expressing E. coli cells (Takakura et al. (2009) FEBS J 276: 1383-1397) was diluted with 0.1 M HEPES/KOH (pH 7.4) to give a total soluble protein concentration of 5 mg/ml, to which the biotinylated magnetic beads were then added. By mixing end-over-end at room temperature for 1 hour, TM2 was immobilized through tamavidin-biotin binding. After washing in the same manner as shown above, the TM2-immobilized magnetic beads thus completed (30 mg beads/mL PBS) were used for subtraction of non-specific binding inherent to serum samples.

4-6. ELISA Analysis Using Magnetic Beads

To commercially available human serum (Human Serum pool, Cosmo-Bio), the same rabbit anti-SITH-1 antibody as used in Example 2 was added in a 1/50 volume to prepare SITH-1 antibody-containing human serum. On the other hand, human serum free from SITH-1 antibody was used as a control.

The human serum or rabbit SITH-1 antibody-containing human serum was diluted 1000-fold with PBS or with the pTrc99A vector product-expressing E. coli crude extract or the TM2-expressing E. coli crude extract, each of which had been adjusted with 0.1 M HEPES/KOH (pH 7.4) to give a total soluble protein concentration of 5 mg/ml. To the resulting solution, BSA was further added at a final concentration of 2% (w/v). In Example 2 described above, human serum was diluted 100-fold and rabbit anti-SITH-1 antibody was then added at a volume ratio of 0.00025 to 0.002 relative to the diluted serum. However, in this Example 4-6, rabbit anti-SITH-1 antibody was added in a 1/50 volume (at a volume ratio of 0.02) to human serum and then diluted 1000-fold. Thus, the dilution factor of the rabbit SITH-1 antibody is 1/50000, which is the same as that of depression patient's serum diluted about 1000-fold.

To the serum dilutions thus prepared (1 mL each), the TM2-fused SITH-1-immobilized magnetic beads or the TM2-immobilized magnetic beads were added in 10 µl volumes and reacted by mixing end-over-end for 1 hour at room temperature, followed by washing three times with TBST. Horseradish peroxidase-labeled goat anti-rabbit IgG antibody (for detection of the rabbit anti-SITH-1 antibody bound to the SITH-1 antigen immobilized on the magnetic beads) and peroxidase-labeled goat anti-human IgG antibody (for detection of human IgG bound non-specifically to the magnetic beads) were each diluted 5000-fold with 2% BSA-containing TBST and then mixed. This peroxidase-labeled secondary antibody mixture was added in 1000 µl volumes to the magnetic beads and mixed end-over-end for 1 hour at room temperature. Then, the beads were further washed three times with TBST, and 100 µl detection reagent (1 step ELISA ultraTMB, PIERCE) was added and reacted at room temperature for 1 minute. 100 µl of 2 M sulfuric acid was added to stop the reaction, and the degree of color development (absorbance at 450 nm wavelength, A450) was measured with a plate reader Infinite M200 (TECAN). The measurement was performed in duplicate for each sample to determine a mean value.

For use as data, the A450 value measured for each serum diluent (PBS, the pTrc99A vector product-expressing E. coli crude extract, or the TM2-expressing E. coli crude extract) in the TM2-fused SITH-1-immobilized magnetic beads was processed by subtraction of the A450 value measured for the corresponding serum diluent in the TM2-immobilized magnetic beads. The results obtained are shown in Table 3.

TABLE 3

Effect of serum diluents on SITH-1 antibody detection in human serum

| | A450 | | |
| --- | --- | --- | --- |
| Serum diluent | Serum containing SITH-1 antibody (S) | Serum free from SITH-1 antibody (N) | S/N ratio |
| PBS | 0.64 | 0.25 | 2.6 |
| pTrc99A-carrying BL21 crude extract | 0.14 | 0.04 | 3.5 |
| TM2/pTrc99A-carrying BL21 crude extract | 0.22 | 0.02 | 11.0 |

As shown in Table 3, the A450 value of SITH-1 antibody in human serum (S) was highest in the case of using PBS as a serum diluent, while the A450 value in serum free from SITH-1 antibody (N) was also very high, thus indicating that the S/N ratio (i.e., the ratio of the degree of color development in human serum containing rabbit anti-SITH-1 antibody to the degree of color development in serum free from rabbit anti-SITH-1 antibody) was lowest in PBS.

In contrast, when the pTrc99A vector product-expressing E. coli crude extract or the TM2-expressing E. coli crude extract was used as a serum diluent, the A450 value in serum free from SITH-1 antibody was much lower than that obtained for PBS, and hence non-specific binding could be greatly suppressed. This indicated that when human serum was mixed with the pTrc99A vector product-expressing E. coli crude extract or with the TM2-expressing E. coli crude extract, it was possible to reduce non-specific binding and detect anti-SITH-1 antibody with the use of the TM2-fused SITH-1-immobilized magnetic beads.

Sequence Listing Free Text

SEQ ID NO: 1: amino acid sequence of SITH-1
SEQ ID NO: 2: nucleotide sequence of SITH-1ORF
SEQ ID NO: 3: nucleotide sequence of SITH-1 cDNA
SEQ ID NO: 4: nucleotide sequence of tamavidin 1
SEQ ID NO: 5: amino acid sequence of tamavidin 1
SEQ ID NO: 6: nucleotide sequence of tamavidin 2
SEQ ID NO: 7: amino acid sequence of tamavidin 2
SEQ ID NO: 8: amino acid sequence of BioEase-SITH-1 fusion protein
SEQ ID NO: 9: nucleotide sequence encoding BioEase-SITH-1 fusion protein
SEQ ID NO: 10: PCR primer SITH1NtermGW-F
SEQ ID NO: 11: PCR primer SITH1NtermGW-R
SEQ ID NO: 12: 5× linker
SEQ ID NO: 13: PCR primer SITH1C-5xlink-TM2N-F
SEQ ID NO: 14: PCR primer SITH1C-5xlink-TM2N-R
SEQ ID NO: 15: PCR primer SITH1C-5' EcoRI-F
SEQ ID NO: 16: PCR primer TM2CtermBam
SEQ ID NO: 17: nucleotide sequence of SITH-1-TM2
SEQ ID NO: 18: amino acid sequence of SITH-1-TM2

The invention claimed is:

1. A method for detecting an antibody against a small protein encoded by the intermediate stage transcript of HHV-6 (SITH-1) in a biological sample, which comprises:
   1) contacting the biological sample with a SITH-1 protein-bound carrier, by adding to the SITH-1 protein-bound carrier a mixture of:
      (a) the biological sample; and
      (b) a cell homogenate extract prepared from cells of the same species as that of host cells used to express the SITH-1 protein; and,
   2) detecting the SITH-1 protein antibody, wherein the SITH-1 protein-bound carrier comprises a SITH-1 protein expressed from a host cell,
wherein the SITH-1 protein is bound to the carrier through binding between biotin and a biotin-binding protein, and
wherein the SITH-1 protein is bound to the carrier by:
   (A) binding of a biotinylated SITH-1 protein to a carrier comprising the biotin-binding protein bound thereto, or
   (B) binding of the biotin-binding protein to a carrier comprising biotin bound thereto, and then binding of a biotinylated SITH-1 protein to the carrier to thus prepare the SITH-1 protein bound carrier.

2. A method for detecting an antibody against a small protein encoded by the intermediate stage transcript of HHV-6 (SITH-1) in a biological sample, which comprises:
   1) contacting the biological sample with a SITH-1 protein-bound carrier, by adding to the SITH-1 protein-bound carrier a mixture of:
      (a) the biological sample; and
      (b-i) a biotin-binding protein in combination with a cell homogenate extract prepared from cells,
         wherein the cells are of the same species as that of host cells used to express any of the SITH-1 protein, the biotinylated SITH-1 protein and/or the biotin-binding protein which constitute the SMITH-1 protein-bound carrier; or
      (b-ii) a cell homogenate extract prepared from cells genetically engineered to express a biotin-binding protein,
         wherein said cells are of the same species as that of host cells used to express any of the SITH-1 protein, the biotinylated SITH-1 protein and/or the biotin-binding protein which constitute the SITH-1 protein-bound carrier; and,
   2) detecting the SITH-1 protein antibody wherein the SITH-1 protein-bound carrier comprises a SITH-1 protein expressed from a host cell,
wherein the SITH-1 protein is bound to the carrier through binding between biotin and a biotin-binding protein, and
wherein the SITH-1 protein is bound to the carrier by:
   (A) binding of a biotinylated SITH-1 protein to a carrier comprising the biotin-binding protein bound thereto, or
   (B) binding of the biotin-binding protein to a carrier comprising biotin bound thereto, and then binding of a biotinylated SITH-1 protein to the carrier to thus prepare the SITH-1 protein bound carrier.

3. The method according to claim 1 or 2, wherein the SITH-1 protein is selected from the group consisting of:
   (a) a protein which has the amino acid sequence of SEQ ID NO: 1;
   (b) a protein which has an amino acid sequence comprising deletion, substitution, insertion and/or addition of one or more amino acids of SEQ ID NO: 1 and which has the ability to increase the intracellular calcium concentration;
   (c) a protein which has an amino acid sequence sharing an identity of at least 80% with SEQ ID) NO: 1 and which has the ability to increase the intracellular calcium concentration;
   (d) a protein which has an amino acid sequence encoded by as nucleic acid consisting of the nucleotide sequence of SEQ ID NO: 2;
   (e) a protein which has an amino acid sequence encoded by a nucleic acid consisting of a nucleotide sequence comprising deletion, substitution, insertion and/or addition of one or more nucleotides in the nucleotide sequence of SEQ ID NO: 2 and which has the ability to increase the intracellular calcium concentration;
   (f) a protein which has an amino acid sequence encoded by a nucleic acid consisting of a nucleotide sequence sharing an identity of 80% or more with SEQ ID NO: 2 and which has the ability to increase the intracellular calcium concentration; and
   (g) a protein which is encoded by a nucleic acid which hybridizes under stringent hybridization conditions with the complement of the nucleotide sequence of SEQ ID NO: 2 and which has the ability to increase the intracellular calcium concentration.

4. The method according to claim 1 or 2, wherein (b) in claim 1 or (b-i) in claim 2 comprises adding, as the cell homogenate extract, a cell homogenate extract extracted from cells comprising a vector
   wherein the vector is selected from:
      (a) an empty vector of the same species as that of the vector used in expression any of the SITH-1 protein, the biotinylated SITH-1 protein, and/or the biotin-binding protein, wherein the vector does not contain a gene which encodes the SITH-1 protein, the biotinylated SITH-1 protein, and/or the biotin-binding protein, (b) the vector of (a) further containing any nucleic acid in the empty vector, or (c) a vector which is different from a vector used in expression of the SITH-1 protein, the biotinylated SITH-1 protein, and/or the biotin-binding protein.

5. The method according to claim 1 or claim 2, wherein the biotin-binding protein is selected from the group consisting of:

(1) a protein comprising the amino acid sequence of SEQ ID NO: 5 or SEQ ID NO: 7;

(2) a protein comprising an amino acid sequence sharing an identity of 80% or more to SEQ ID NO: 5 or SEQ ID NO: 7;

(3) a protein encoded by a nucleic acid comprising SEQ ID NO: 4 or SEQ ID NO: 6; and (4) a protein encoded by a nucleic acid comprising a nucleotide sequence sharing an identity or 80% or more to SEQ ID NO: 4 or SEQ ID NO: 6.

6. The method according to claim 1 or 2, wherein the biological sample is selected from the group consisting of: blood, serum, cerebrospinal fluid, saliva, throat swab, sweat, urine, tear, lymph, semen, peritoneal fluid, and mother's milk.

\* \* \* \* \*

SEQUENCE LISTING

<160> NUMBER OF SEQ ID NOS: 18

<210> SEQ ID NO 1
<211> LENGTH: 159
<212> TYPE: PRT
<213> ORGANISM: Human herpesvirus 6

<400> SEQUENCE: 1

Met Gly Tyr Glu Glu Lys Val Ser Ala Thr Gly Lys Thr Arg Leu Lys
1               5                   10                  15

Ile Leu Ala Cys Leu Ile Val Leu Ile Leu Ala Ala Ala Ile Thr Met
            20                  25                  30

Leu Thr Leu Glu Ile Ile Ser Asn Gln Lys Arg Thr Thr Thr Asp Leu
        35                  40                  45

Glu Ala Val Thr Val Ala Leu Lys His Val Ser Thr Ser Leu Ala Ser
    50                  55                  60

Cys Thr Glu Ser Thr Thr Ser Val His Thr Asp Ser Val Thr Ser Gln
65                  70                  75                  80

Pro Thr Lys Asn Lys Glu Ser Arg Lys Lys Ile Glu Gly Lys Ser Pro
                85                  90                  95

Ser Trp Val Gln Ala Leu Thr Thr Ala Ser Gly Ile Ile Leu Leu Phe
            100                 105                 110

Cys Ile Met Met Ile Phe Ile Thr Cys Ser Trp Thr Thr Glu Lys Asp
        115                 120                 125

Thr Glu Lys Ser Glu Val Gln Ser Tyr Ala Ser Ser Val Glu Thr Leu
    130                 135                 140

Asp Ser Leu Asn Glu Ala Ile Ile Pro Lys Thr Glu Met Asn Val
145                 150                 155

<210> SEQ ID NO 2
<211> LENGTH: 480
<212> TYPE: DNA
<213> ORGANISM: Human herpesvirus 6

<400> SEQUENCE: 2
atgggatatg aagaaaaagt gtcagctact ggaaagactc gtttaaagat actggcatgt      60
ctgatcgttt taatactagc tgcggcaata actatgttaa cgctggaaat tatatcgaac     120
caaaaacgta ccactactga tctcgaagct gtgactgtgg cgctgaagca tgtaagcaca     180
tctcttgcca gctgcactga atccactact tctgtacata ccgattctgt gacgagccaa     240
cccacgaaaa acaaagaatc gaggaaaaaa attgaaggga atctccaag ttgggttcag      300 gcttttaacta cagcatctgg aattatccta ctgttttgta taatgatgat attcattaca     360
tgttcctgga ccacagaaaa agatacagag aagagtgaag tgcaatctta tgcttcttca     420
gtagagactt tagactcttt aaatgaggct attataccga aaactgaaat gaatgtgtaa     480

<210> SEQ ID NO 3
<211> LENGTH: 1795
<212> TYPE: DNA
<213> ORGANISM: Human herpesvirus 6

<400> SEQUENCE: 3
aggctctgct ggaggctctg ctggaggcct tgctgaaggc tctgctggag gccctgctgg      60
aggtcttgct ggaggctctg ctggaggctc tgctggaggc tctgctggag gctctgctgg     120
aggctctgct ggaggctctg ctggaggctc tgtcagagac ctcggtgaaa gttttactca     180
gaggtttatc agagttttcg ccattagttt ggttagaagt ttcagattta ttttcggtgg     240
aactgcagtt aggtttcatg tcagtacatt catcaccgtt agaagtgcta ttcatggtgc     300
tgttgccact gttggatttg ttaaaagcag taaatgagct aggattggaa tgactccgaa     360
tagctaataa atttgagcat tttcttcgaa tggatcataa tcagagggat agccatctaa     420

-continued

```
tttaaagact tccattttat cactgttgca atcacttcta atggagtatc tggatacatt    480
ttttctacat cttttcatc ccctccaaca tggatctgtg cagcgttaat aagccagcgg    540
agttaattaa atcgtcttcc atgttagaca gttcctgttt catggcagcc ttcactgatg    600
caccaatact ttggatgcaa gtgccaacgg actgagctag gatgtaaaag aagatattct    660
aattttgaat tcttcagatg ctccttcttc cacattactg aataggaca cattcttgga    720 agcgatgtcg ttggaagact ctgggatgaa aagatcacag gcttccagtt ctggaaaaag    780
caggctttca aaggacacat cacacttgag actctcttcc aatatttctt tgatggattc    840
ttccaccact ggatcgggat ggtagctata tatactatat aaggagatta ccaccaccac    900
ctctttcttt gcagagatta ttctctgctt gaaaatctgt aacactgatc atgatgggat    960
atgaagaaaa agtgtcagct actgaaaaga ctcgttaaa gatactggca tgtctgatcg   1020
ttttaatact agctgcggca ataactatgt taacgctgga attatatcg aaccaaaaac   1080 gtaccactac tgatctcgaa gctgtgactg tggcgctgaa gcatgtaagc acatctcttg   1140
ccagctgcac tgaatccact acttctgtac ataccgattc tgtgacgagc caacccacga   1200
aaaacaaaga atcgaggaaa aaattgaag ggaaatctcc aagttgggtt caggctttaa   1260
ctacagcatc tggaattatc ctactgtttt gtataatgat gatattcatt acatgtccct   1320
ggaccacaga aaaagataca gagaagagtg aagtgcaatc ttatgctcct tcagtagaga   1380
ctttagaccc tttaaatgag gctattatac cgaaaactga atgaatgtg taatgtctgt   1440 atttttcttt acagagatgt acggagagtt tatatttggg gaaataccct gactgttctg   1500
cctatatgcg aatgttaaag tatgtataat ataaattctt accttttaag agtgattcaa   1560
ggtggaggtt tctttggaga ttgattccag gtggtggttt cgggtgcaat caatctttct   1620
tctgggcggg aagaaaatcc agcaatccaa taattgatgg gatgtaatca atgtcacaaa   1680
tctgtaagat taaatgtgaa cagtataaat tctttcgtgc ttatcaaatt acaattatgc   1740
gcatgaaaat atcattaaat tgttttaaac attcttaaaa aaaaaaaaaa aaaaa         1795
```

```
<210> SEQ ID NO 4
<211> LENGTH: 432
<212> TYPE: DNA
<213> ORGANISM: Pleurotus cornucopiae
<220> FEATURE:
<221> NAME/KEY: CDS
<222> LOCATION: (1)..(432)

<400> SEQUENCE: 4 atg aaa gac gtc caa tct ctc ctc acc gga acc tgg tac aat gaa ctc    48
Met Lys Asp Val Gln Ser Leu Leu Thr Gly Thr Trp Tyr Asn Glu Leu
 1               5                  10                  15 ggc tca aca atg aat ttg act gca aat aaa gac ggt tcg ctc acc gga    96
Gly Ser Thr Met Asn Leu Thr Ala Asn Lys Asp Gly Ser Leu Thr Gly
             20                  25                  30 acg tac cac tcc aac gtc ggc gag gtt ccc cca act tat cac ctt tct   144
Thr Tyr His Ser Asn Val Gly Glu Val Pro Pro Thr Tyr His Leu Ser
         35                  40                  45 ggc cgg tac aac ctc cag ccc ccc tcg ggt caa ggc gtt act ctg gga   192
Gly Arg Tyr Asn Leu Gln Pro Pro Ser Gly Gln Gly Val Thr Leu Gly
     50                  55                  60 tgg gcg gtg tct ttc gaa aac act agt gcg aat gtt cat tct gtc tca   240
Trp Ala Val Ser Phe Glu Asn Thr Ser Ala Asn Val His Ser Val Ser
 65                  70                  75                  80 aca tgg agc ggg cag tac ttc tct gaa ccc gcc gag gtg atc ctc acc   288
Thr Trp Ser Gly Gln Tyr Phe Ser Glu Pro Ala Glu Val Ile Leu Thr
```

```
                    85                  90                  95
cag tgg ctg ttg tca agg agc tct gag cgc gaa gat ttg tgg cag tcc        336
Gln Trp Leu Leu Ser Arg Ser Ser Glu Arg Glu Asp Leu Trp Gln Ser
            100                 105                 110 acc cat gtg ggg cat gat gag ttc agc aag aca aag cca acc aag gag        384
Thr His Val Gly His Asp Glu Phe Ser Lys Thr Lys Pro Thr Lys Glu
        115                 120                 125 aag att gcc cag gct caa ctc ctt cgt cgc ggg ttg aag ttc gag tga        432
Lys Ile Ala Gln Ala Gln Leu Leu Arg Arg Gly Leu Lys Phe Glu
    130                 135                 140

<210> SEQ ID NO 5
<211> LENGTH: 143
<212> TYPE: PRT
<213> ORGANISM: Pleurotus cornucopiae

<400> SEQUENCE: 5

Met Lys Asp Val Gln Ser Leu Leu Thr Gly Thr Trp Tyr Asn Glu Leu
1               5                   10                  15

Gly Ser Thr Met Asn Leu Thr Ala Asn Lys Asp Gly Ser Leu Thr Gly
            20                  25                  30

Thr Tyr His Ser Asn Val Gly Glu Val Pro Pro Thr Tyr His Leu Ser
        35                  40                  45

Gly Arg Tyr Asn Leu Gln Pro Pro Ser Gly Gln Gly Val Thr Leu Gly
    50                  55                  60

Trp Ala Val Ser Phe Glu Asn Thr Ser Ala Asn Val His Ser Val Ser
65                  70                  75                  80

Thr Trp Ser Gly Gln Tyr Phe Ser Glu Pro Ala Glu Val Ile Leu Thr
                85                  90                  95

Gln Trp Leu Leu Ser Arg Ser Ser Glu Arg Glu Asp Leu Trp Gln Ser
            100                 105                 110

Thr His Val Gly His Asp Glu Phe Ser Lys Thr Lys Pro Thr Lys Glu
        115                 120                 125

Lys Ile Ala Gln Ala Gln Leu Leu Arg Arg Gly Leu Lys Phe Glu
    130                 135                 140

<210> SEQ ID NO 6
<211> LENGTH: 426
<212> TYPE: DNA
<213> ORGANISM: Pleurotus cornucopiae
<220> FEATURE:
<221> NAME/KEY: CDS
<222> LOCATION: (1)..(426)

<400> SEQUENCE: 6 atg tca gac gtt caa tct tca ctc acc gga acc tgg tac aat gaa ctc         48
Met Ser Asp Val Gln Ser Ser Leu Thr Gly Thr Trp Tyr Asn Glu Leu
1               5                   10                  15 aac tcc aag atg gaa ttg act gca aac aaa gac ggt act ctc act gga         96
Asn Ser Lys Met Glu Leu Thr Ala Asn Lys Asp Gly Thr Leu Thr Gly
            20                  25                  30 aag tac ctc tcc aaa gtt ggg gat gtc tac gtg ccc tac cca ctc tct        144
Lys Tyr Leu Ser Lys Val Gly Asp Val Tyr Val Pro Tyr Pro Leu Ser
        35                  40                  45 ggt cgc tat aac ctc caa ccc ccc gcg gga caa ggc gtc gct ctt ggg        192
Gly Arg Tyr Asn Leu Gln Pro Ala Gly Gln Gly Val Ala Leu Gly
    50                  55                  60 tgg gcg gta tcc tgg gag aac agt aaa att cat tcc gct acg aca tgg        240
Trp Ala Val Ser Trp Glu Asn Ser Lys Ile His Ser Ala Thr Thr Trp
65                  70                  75                  80
```

-continued

```
agc gga cag ttc ttc tct gag tcg tct cca gtg att ctt act cag tgg    288
Ser Gly Gln Phe Phe Ser Glu Ser Ser Pro Val Ile Leu Thr Gln Trp
            85                  90                  95 ttg ttg tca tcg agc act gcg cgt ggg gac gta tgg gaa tcc aca ctt    336
Leu Leu Ser Ser Ser Thr Ala Arg Gly Asp Val Trp Glu Ser Thr Leu
            100                 105                 110 gtg ggg aat gat tcg ttt aca aag acg gcg ccg act gag cag cag atc    384
Val Gly Asn Asp Ser Phe Thr Lys Thr Ala Pro Thr Glu Gln Gln Ile
            115                 120                 125 gct cat gct caa ctc cat tgt cgc gca ccg agg ttg aag taa            426
Ala His Ala Gln Leu His Cys Arg Ala Pro Arg Leu Lys
            130                 135                 140
```

<210> SEQ ID NO 7
<211> LENGTH: 141
<212> TYPE: PRT
<213> ORGANISM: Pleurotus cornucopiae

<400> SEQUENCE: 7

```
Met Ser Asp Val Gln Ser Ser Leu Thr Gly Thr Trp Tyr Asn Glu Leu
1               5                   10                  15

Asn Ser Lys Met Glu Leu Thr Ala Asn Lys Asp Gly Thr Leu Thr Gly
            20                  25                  30

Lys Tyr Leu Ser Lys Val Gly Asp Val Tyr Val Pro Tyr Pro Leu Ser
            35                  40                  45

Gly Arg Tyr Asn Leu Gln Pro Pro Ala Gly Gln Gly Val Ala Leu Gly
            50                  55                  60

Trp Ala Val Ser Trp Glu Asn Ser Lys Ile His Ser Ala Thr Thr Trp
65                  70                  75                  80

Ser Gly Gln Phe Phe Ser Glu Ser Ser Pro Val Ile Leu Thr Gln Trp
            85                  90                  95

Leu Leu Ser Ser Ser Thr Ala Arg Gly Asp Val Trp Glu Ser Thr Leu
            100                 105                 110

Val Gly Asn Asp Ser Phe Thr Lys Thr Ala Pro Thr Glu Gln Gln Ile
            115                 120                 125

Ala His Ala Gln Leu His Cys Arg Ala Pro Arg Leu Lys
            130                 135                 140
```

<210> SEQ ID NO 8
<211> LENGTH: 271
<212> TYPE: PRT
<213> ORGANISM: Artificial Sequence
<220> FEATURE:
<223> OTHER INFORMATION: Synthetic fusion protein BioEase Tag-SITH-1

<400> SEQUENCE: 8

```
Met Ala Ser Met Thr Gly Gly Gln Gln Met Gly Ile Met Gly Ala Gly
1               5                   10                  15

Thr Pro Val Thr Ala Pro Leu Ala Gly Thr Ile Trp Lys Val Leu Ala
            20                  25                  30

Ser Glu Gly Gln Thr Val Ala Ala Gly Glu Val Leu Leu Ile Leu Glu
            35                  40                  45

Ala Met Lys Met Glu Thr Glu Ile Arg Ala Ala Gln Ala Gly Thr Val
            50                  55                  60

Arg Gly Ile Ala Val Lys Ala Gly Asp Ala Val Ala Val Gly Asp Thr
65                  70                  75                  80

Leu Met Thr Leu Ala Gly Ser Gly Ser Asp Leu Tyr Asp Asp Asp Asp
            85                  90                  95
```

```
Lys Gly Ile Ile Thr Ser Leu Tyr Lys Lys Ala Gly Ser Glu Phe Ala
            100                 105                 110
Leu Gly Tyr Glu Glu Lys Val Ser Ala Thr Gly Lys Thr Arg Leu Lys
        115                 120                 125
Ile Leu Ala Cys Leu Ile Val Leu Ile Leu Ala Ala Ile Thr Met
    130                 135                 140
Leu Thr Leu Glu Ile Ile Ser Asn Gln Lys Arg Thr Thr Thr Asp Leu
145                 150                 155                 160
Glu Ala Val Thr Val Ala Leu Lys His Val Ser Thr Ser Leu Ala Ser
                165                 170                 175
Cys Thr Glu Ser Thr Thr Ser Val His Thr Asp Ser Val Thr Ser Gln
            180                 185                 190
Pro Thr Lys Asn Lys Glu Ser Arg Lys Lys Ile Glu Gly Lys Ser Pro
        195                 200                 205
Ser Trp Val Gln Ala Leu Thr Thr Ala Ser Gly Ile Ile Leu Leu Phe
    210                 215                 220
Cys Ile Met Met Ile Phe Ile Thr Cys Ser Trp Thr Thr Glu Lys Asp
225                 230                 235                 240
Thr Glu Lys Ser Glu Val Gln Ser Tyr Ala Ser Ser Val Glu Thr Leu
                245                 250                 255
Asp Ser Leu Asn Glu Ala Ile Ile Pro Lys Thr Glu Met Asn Val
            260                 265                 270

<210> SEQ ID NO 9
<211> LENGTH: 816
<212> TYPE: DNA
<213> ORGANISM: Artificial Sequence
<220> FEATURE:
<223> OTHER INFORMATION: DNA encoding fusion protein BioEase Tag-SITH-1

<400> SEQUENCE: 9
atggctagca tgactggtgg acagcaaatg ggtattatgg cgccggcac cccggtgacc      60
gccccgctgg cgggcactat ctggaaggtg ctggccagcg aaggccagac ggtggccgca     120
ggcgaggtgc tgctgattct ggaagccatg aagatggaaa ccgaaatccg cgccgcgcag     180
gccgggaccg tgcgcggtat cgcggtgaaa gccggcgacg cggtggcggt cggcgacacc     240
ctgatgaccc tggcgggctc tggatccgat ctgtacgacg atgacgataa gggaattatc     300
acaagtttgt acaaaaaagc aggctccgaa ttcgcccttg atatgaaga aaaagtgtca     360
gctactggaa agactcgttt aaagatactg gcatgtctga tcgttttaat actagctgcg     420
gcaataacta tgttaacgct ggaaattata tcgaaccaaa aacgtaccac tactgatctc     480
gaagctgtga ctgtggcgct gaagcatgta agcacatctc ttgccagctg cactgaatcc     540
actacttctg tacataccga ttctgtgacg agccaaccca cgaaaaacaa agaatcgagg     600
aaaaaaattg aagggaaatc tccaagttgg gttcaggctt taactacagc atctggaatt     660
atcctactgt tttgtataat gatgatattc attacatgtt cctggaccac agaaaaagat     720
acagagaaga gtgaagtgca atcttatgct tcttcagtag agactttaga ctctttaaat     780
gaggctatta taccgaaaac tgaaatgaat gtgtaa                               816

<210> SEQ ID NO 10
<211> LENGTH: 20
<212> TYPE: DNA
<213> ORGANISM: Artificial Sequence
<220> FEATURE:
<223> OTHER INFORMATION: Synthetic primer SITH1NtermGW-F
```

```
<400> SEQUENCE: 10
ggatatgaag aaaaagtgtc                                                    20

<210> SEQ ID NO 11
<211> LENGTH: 20
<212> TYPE: DNA
<213> ORGANISM: Artificial Sequence
<220> FEATURE:
<223> OTHER INFORMATION: Synthetic primer SITH1CtermGW-R

<400> SEQUENCE: 11
ttacacattc atttcagttt                                                    20

<210> SEQ ID NO 12
<211> LENGTH: 25
<212> TYPE: PRT
<213> ORGANISM: Artificial Sequence
<220> FEATURE:
<223> OTHER INFORMATION: Synthetic peptide linker

<400> SEQUENCE: 12

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 13
<211> LENGTH: 117
<212> TYPE: DNA
<213> ORGANISM: Artificial Sequence
<220> FEATURE:
<223> OTHER INFORMATION: Synthetic primer SITH1C-5xlink-TM2N-F

<400> SEQUENCE: 13
ccgaaaactg aaatgaatgt gggtggcggt ggcagcggtg gcggtggcag cggtggcggt      60
ggcagcggtg gcggtggcag cggtggcggt ggcagctcag acgttcaatc ttcactc        117

<210> SEQ ID NO 14
<211> LENGTH: 117
<212> TYPE: DNA
<213> ORGANISM: Artificial Sequence
<220> FEATURE:
<223> OTHER INFORMATION: Synthetic primer SITH1C-5xlink-TM2N-R

<400> SEQUENCE: 14
gagtgaagat tgaacgtctg agctgccacc gccaccgctg ccaccgccac cgctgccacc      60
gccaccgctg ccaccgccac cgctgccacc gccacccaca ttcatttcag ttttcgg       117

<210> SEQ ID NO 15
<211> LENGTH: 29
<212> TYPE: DNA
<213> ORGANISM: Artificial Sequence
<220> FEATURE:
<223> OTHER INFORMATION: Synthetic primer SITH1C-5' EcoRI-F

<400> SEQUENCE: 15
aaagaattcg gatatgaaga aaaagtgtc                                          29

<210> SEQ ID NO 16
<211> LENGTH: 28
<212> TYPE: DNA
<213> ORGANISM: Artificial Sequence
<220> FEATURE:
```

<223> OTHER INFORMATION: Synthetic primer TM2CtermBam

<400> SEQUENCE: 16
tttggatcct tacttcaacc tcggtgcg                                28

<210> SEQ ID NO 17
<211> LENGTH: 981
<212> TYPE: DNA
<213> ORGANISM: Artificial Sequence
<220> FEATURE:
<223> OTHER INFORMATION: DNA encoding fusion protein SITH-1-TM2
<220> FEATURE:
<221> NAME/KEY: CDS
<222> LOCATION: (1)..(978)

<400> SEQUENCE: 17

```
atg gaa ttc gga tat gaa gaa aaa gtg tca gct act gga aag act cgt      48
Met Glu Phe Gly Tyr Glu Glu Lys Val Ser Ala Thr Gly Lys Thr Arg
1               5                   10                  15 tta aag ata ctg gca tgt ctg atc gtt tta ata cta gct gcg gca ata      96
Leu Lys Ile Leu Ala Cys Leu Ile Val Leu Ile Leu Ala Ala Ala Ile
            20                  25                  30 act atg tta acg ctg gaa att ata tcg aac caa aaa cgt acc act act     144
Thr Met Leu Thr Leu Glu Ile Ile Ser Asn Gln Lys Arg Thr Thr Thr
        35                  40                  45 gat ctc gaa gct gtg act gtg gcg ctg aag cat gta agc aca tct ctt     192
Asp Leu Glu Ala Val Thr Val Ala Leu Lys His Val Ser Thr Ser Leu
    50                  55                  60 gcc agc tgc act gaa tcc act act tct gta cat acc gat tct gtg acg     240
Ala Ser Cys Thr Glu Ser Thr Thr Ser Val His Thr Asp Ser Val Thr
65                  70                  75                  80 agc caa ccc acg aaa aac aaa gaa tcg agg aaa aaa att gaa ggg aaa     288
Ser Gln Pro Thr Lys Asn Lys Glu Ser Arg Lys Lys Ile Glu Gly Lys
                85                  90                  95 tct cca agt tgg gtt cag gct tta act aca gca tct gga att atc cta     336
Ser Pro Ser Trp Val Gln Ala Leu Thr Thr Ala Ser Gly Ile Ile Leu
            100                 105                 110 ctg ttt tgt ata atg atg ata ttc att aca tgt tcc tgg acc aca gaa     384
Leu Phe Cys Ile Met Met Ile Phe Ile Thr Cys Ser Trp Thr Thr Glu
        115                 120                 125 aaa gat aca gag aag agt gaa gtg caa tct tat gct tct tca gta gag     432
Lys Asp Thr Glu Lys Ser Glu Val Gln Ser Tyr Ala Ser Ser Val Glu
    130                 135                 140 act tta gac tct tta aat gag gct att ata ccg aaa act gaa atg aat     480
Thr Leu Asp Ser Leu Asn Glu Ala Ile Ile Pro Lys Thr Glu Met Asn
145                 150                 155                 160 gtg ggt ggc ggt ggc agc ggt ggc ggt ggc agc ggt ggc ggt ggc agc     528
Val Gly Gly Gly Gly Ser Gly Gly Gly Gly Ser Gly Gly Gly Gly Ser
                165                 170                 175 ggt ggc ggt ggc agc ggt ggc ggt ggc agc tca gac gtt caa tct tca     576
Gly Gly Gly Gly Ser Gly Gly Gly Gly Ser Ser Asp Val Gln Ser Ser
            180                 185                 190 ctc acc gga acc tgg tac aat gaa ctc aac tcc aag atg gaa ttg act     624
Leu Thr Gly Thr Trp Tyr Asn Glu Leu Asn Ser Lys Met Glu Leu Thr
        195                 200                 205 gca aac aaa gac ggt act ctc act gga aag tac ctc tcc aaa gtt ggg     672
Ala Asn Lys Asp Gly Thr Leu Thr Gly Lys Tyr Leu Ser Lys Val Gly
    210                 215                 220 gat gtc tac gtg ccc tac cca ctc tct ggt cgc tat aac ctc caa ccc     720
Asp Val Tyr Val Pro Tyr Pro Leu Ser Gly Arg Tyr Asn Leu Gln Pro
225                 230                 235                 240
```

| | | |
|---|---|---|
| ccc gcg gga caa ggc gtc gct ctt ggg tgg gcg gta tcc tgg gag aac<br>Pro Ala Gly Gln Gly Val Ala Leu Gly Trp Ala Val Ser Trp Glu Asn<br>245 250 255 | | 768 |
| agt aaa att cat tcc gct acg aca tgg agc gga cag ttc ttc tct gag<br>Ser Lys Ile His Ser Ala Thr Thr Trp Ser Gly Gln Phe Phe Ser Glu<br>260 265 270 | | 816 |
| tcg tct cca gtg att ctt act cag tgg ttg ttg tca tcg agc act gcg<br>Ser Ser Pro Val Ile Leu Thr Gln Trp Leu Leu Ser Ser Ser Thr Ala<br>275 280 285 | | 864 |
| cgt ggg gac gta tgg gaa tcc aca ctt gtg ggg aat gat tcg ttt aca<br>Arg Gly Asp Val Trp Glu Ser Thr Leu Val Gly Asn Asp Ser Phe Thr<br>290 295 300 | | 912 |
| aag acg gcg ccg act gag cag cag atc gct cat gct caa ctc cat tgt<br>Lys Thr Ala Pro Thr Glu Gln Gln Ile Ala His Ala Gln Leu His Cys<br>305 310 315 320 | | 960 |
| cgc gca ccg agg ttg aag taa<br>Arg Ala Pro Arg Leu Lys<br>325 | | 981 |

<210> SEQ ID NO 18
<211> LENGTH: 326
<212> TYPE: PRT
<213> ORGANISM: Artificial Sequence
<220> FEATURE:
<223> OTHER INFORMATION: Synthetic fusion protein SITH-1-TM2

<400> SEQUENCE: 18

Met Glu Phe Gly Tyr Glu Glu Lys Val Ser Ala Thr Gly Lys Thr Arg
1               5                   10                  15

Leu Lys Ile Leu Ala Cys Leu Ile Leu Ile Leu Ala Ala Ala Ile
            20                  25                  30

Thr Met Leu Thr Leu Glu Ile Ile Ser Asn Gln Lys Arg Thr Thr Thr
        35                  40                  45

Asp Leu Glu Ala Val Thr Val Ala Leu Lys His Val Ser Thr Ser Leu
    50                  55                  60

Ala Ser Cys Thr Glu Ser Thr Thr Ser Val His Thr Asp Ser Val Thr
65                  70                  75                  80

Ser Gln Pro Thr Lys Asn Lys Glu Ser Arg Lys Ile Glu Gly Lys
            85                  90                  95

Ser Pro Ser Trp Val Gln Ala Leu Thr Thr Ala Ser Gly Ile Ile Leu
            100                 105                 110

Leu Phe Cys Ile Met Met Ile Phe Ile Thr Cys Ser Trp Thr Thr Glu
        115                 120                 125

Lys Asp Thr Glu Lys Ser Glu Val Gln Ser Tyr Ala Ser Ser Val Glu
    130                 135                 140

Thr Leu Asp Ser Leu Asn Glu Ala Ile Ile Pro Lys Thr Glu Met Asn
145                 150                 155                 160

Val Gly Gly Gly Ser Gly Gly Gly Ser Gly Gly Gly Ser
            165                 170                 175

Gly Gly Gly Gly Ser Gly Gly Gly Ser Ser Asp Val Gln Ser Ser
            180                 185                 190

Leu Thr Gly Thr Trp Tyr Asn Glu Leu Asn Ser Lys Met Glu Leu Thr
        195                 200                 205

Ala Asn Lys Asp Gly Thr Leu Thr Gly Lys Tyr Leu Ser Lys Val Gly
    210                 215                 220

Asp Val Tyr Val Pro Tyr Pro Leu Ser Gly Arg Tyr Asn Leu Gln Pro
225                 230                 235                 240

-continued

```
Pro Ala Gly Gln Gly Val Ala Leu Gly Trp Ala Val Ser Trp Glu Asn
                245                 250                 255
Ser Lys Ile His Ser Ala Thr Thr Trp Ser Gly Gln Phe Phe Ser Glu
            260                 265                 270
Ser Ser Pro Val Ile Leu Thr Gln Trp Leu Leu Ser Ser Ser Thr Ala
        275                 280                 285
Arg Gly Asp Val Trp Glu Ser Thr Leu Val Gly Asn Asp Ser Phe Thr
    290                 295                 300
Lys Thr Ala Pro Thr Glu Gln Gln Ile Ala His Ala Gln Leu His Cys
305                 310                 315                 320
Arg Ala Pro Arg Leu Lys
                325
```